United States Patent [19]
Watanabe et al.

[11] Patent Number: 5,569,650
[45] Date of Patent: Oct. 29, 1996

[54] C-NUCLEOSIDE ISOSTERS OF ANALOGS THEREOF AND PHARMACEUTICAL COMPOSITIONS

[75] Inventors: Kyoichi A. Watanabe, Rye-Brook; Krzystof W. Pankiewicz, Bronxville; Barry M. Goldstein, Rochester, all of N.Y.; J. Ellis Bell, Saint Peters, Minn.

[73] Assignees: Sloan-Kettering Institute for Cancer Research, New York; The University of Rochester, Monroe, both of N.Y.

[21] Appl. No.: 75,746

[22] Filed: Jun. 11, 1993

[51] Int. Cl.$^6$ .................... A61K 31/70; C07H 19/207
[52] U.S. Cl. .................... 514/43; 514/47; 536/26.24
[58] Field of Search ................... 536/26.40, 26.20, 536/25.33; 514/43, 47

[56] References Cited

U.S. PATENT DOCUMENTS

| | | | |
|---|---|---|---|
| 3,266,989 | 8/1966 | O'Hollaren | 514/47 |
| 4,008,363 | 2/1977 | Re et al. | 536/26.24 |
| 4,088,639 | 5/1978 | Zappelli et al. | 536/26.24 |
| 4,443,594 | 4/1984 | Buckmann | 536/26.24 |
| 4,950,602 | 8/1990 | Cooper | 435/184 |

FOREIGN PATENT DOCUMENTS

| | | | |
|---|---|---|---|
| 3936802 | 5/1991 | Germany | 536/26.24 |
| 0096610 | 5/1985 | Japan | 536/26.24 |
| 2067096 | 3/1987 | Japan | 536/26.24 |

OTHER PUBLICATIONS

Tonooka et al., "Synthesis of Isonicotinic Acid Hydrazide (INH)—and Isonicotinic Acid (INA)–Analogs of NAD," *Hokkaido Daigaku Meneki Kagaku Kenkyusho Kiyo*, 37, pp. 14–18(1977); Chem. Abstr., 87(23), p. 221, Abstract No. 1789705e (1977); Only abstract supplied.

Fujisawa et al., "Application of Nicotinamide–Adenine Dinucleotide Analogs for Clinical Enzymology: Alchohol Dehydrogenase Activity in Liver Injury," *Clin. Chim. Acta*, 69(2), 251–257 (1976); Chem. Abstr., 85(7), p. 212, Abstract No. 42681h (1976); Only abstract supplied.

Danenberg et al., "The Interaction of Liver Alchohol Dehydrogenase With Phenyl Adenine Dinucleotide, a Novel Analog of Pyridine Nucleotide Coenzymes," *J. Biol. Chem.*, 253(17), 5886–5887 (1978).

Riley et al., "Synthesis of 2–(β–D–Ribofuranosyl)pyrimidines, A New Class of C–Nucleosides," *J. Heterocyclic Chem.* 24, 955–964 (1987).

Pankiewicz et al.(I), "Synthesis of Isosteric Analogues of Nicotinamide Adenine Dinucleotide Containing C–Nucleotide of Nicotinamide or Picolinamide," *J. Medicinal Chem.*, 36(3), 1855–1859 (1993).

Goldstein et al.(I), "CNAD: A Potent and Specific Inhibitor of Alcohol Dehydrogenase," *J. Medicinal Chem.*, 37(3), 392–399 (1994).

Kandel et al., "Interaction of Fragment A from Diphtheria Toxin With Nicotinamide Adenine Dinucleotide," *J. Biol. Chem.*, 249(7), 2088–2097 (1974).

Favilla et al., "The Binding of 1,N$^6$–ethenoNAD to Bovine Liver Glutamate Dehydrogenase: Studies Using the Time–Correlated Single Photon Counting Fluorescence Technique," *Biochim. Biophys. Acta*, 870, 41–49 (1986).

Moss et al., "Stimulation of Thiol–Dependent ADP–Ribosyl Transferase and NAD Glycohydrolase Activities of *Bordetella pertussis* Toxin by Adenine Nucleotides, Phospholipids, and Detergents," *Biochemistry*, 25(9), 2720–2725 (1986).

Yoshikawa et al., "A Novel Method for Phosphorylation of Nucleosides to 5'–Nucleotides," *Tett. Lett.*, 19, 5065–5068 (1967).

Pankiewicz et al.(II), "Efficient Synthesis of 5–(β–D–Ribofuranosyl)nucotinamide and Its α–Isomer," *J. Org. Chem.*, 53(15) 3473–3479 (1988).

Kabat et al.(I), "Nucleosides, CXLVIII. Synthesis of 6–(β–D–Ribofuranosyl)picolinamide. A Novel C–Nucleoside from D–Ribonolactone," *Chem. Pharm. Bull.*, 36(2), 634–640 (1988).

Kabat et al.,(II), "Synthesis of 5–β–D–Ribofuranosylnicotinamide and Its N–Methyl Derivative. The Isosteric and Isoelectronic Analogues of Nicotinamide Nucleoside," *J. Med. Chem.*, 30(5), 924–927 (1987).

Goldstein et al.(II), "Dehydrogenase Binding by Tiazofurin Anabolites," *J. Med. Chem.*, 33(4), 1123–1127 (1990).

Kabat et al.(III), "Synthesis of C–Nucleoside Isosteres of Nicotinamide Nucleoside," Presentation at Am. Chem. Soc. Convention, Anaheim CA, Sep. 7–12, 1986, see abstract No. 89.

(List continued on next page.)

*Primary Examiner*—John Kight
*Assistant Examiner*—L. Eric Crane
*Attorney, Agent, or Firm*—John P. White

[57] ABSTRACT

This invention provides a compound having the structure:

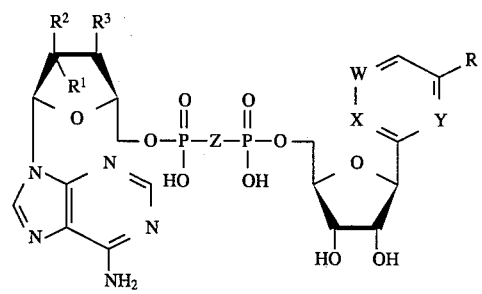

wherein $R^1$, $R^2$, and $R^3$ are same or different, and are hydrogen, hydroxyl, or fluorine; Z is O, $CH_2$ or $CF_2$; R is chlorine, bromine, iodine, carbonitrile, carboxylic ester, or carboxamide; and one of W, X and Y is N or $N^+R'$, wherein R' is methyl or ethyl, and all others are CH; provided that $R^1$ is not H when $R^2$ and $R^3$ are OH, Z is O, R is carboxamide and W is N or $N^+R'$.

This invention also provides methods of preparing the compounds and a method of treating a mammal having a NAD-dependent enzyme associated disorder.

4 Claims, No Drawings

OTHER PUBLICATIONS

Kabat et al.(IV), "Synthesis of 5–Bromo–3–(ribofuranosyl)–pyridine," Presentation at Am. Chem. Soc. Convention, New York, NY, Apr. 13–18, 1986, see abstract No. 2.

Berger et al., "Modulation of Nicotinamide Adenine Dinucleotide and Poly(Adenosine Diphosphoribose) Metabolism by the Synthetic C Nucleoside Analogs, Tiazofurin and Selenazofurin," *J. Clinical Invest.*, 75(2), 702–709 (1985).

Gebeyehu et al., "Synthesis of Thiazolo–4–carboxamide Adenine Dinucleotide. A Powerful Inhibitor of IMP Dehydrogenase," *J. Medicinal Chem.*, 26(6), 922–925 (1983).

Gebeyehu et al., (II) "Ribavirin, Tiazofurin, and Selenazofurin: Mononucleotides and Nicotinamide Adenine Dinucleotide Analogues. Synthesis, Structure, and Interactions with IMP Dehydrogenase," *J. Medicinal Chem.*, 28(1), 99–105 (1985).

Buzik et al., *Elsevier Science Publishers, Amsterdam, The Netherlands*, pp. 231–234 (1986);.

M. Fieser, *John Wiley & Sons, New York*, vol. 8, p. 489 (1980); and.

Ikehara et al., Advances in Chemistry and Biochemistry, vo. 36, pp. 180–192 (1979).

C-NUCLEOSIDE ISOSTERS OF ANALOGS THEREOF AND PHARMACEUTICAL COMPOSITIONS

The invention described herein was made in the course of work under Grant No. CA 33907 from the National Cancer Institute, National Institutes of Health, U.S. Department of Health and Human Services. The U.S. Government has certain rights in this invention.

BACKGROUND OF THE INVENTION

The pyridine C-nucleoside having the structure:

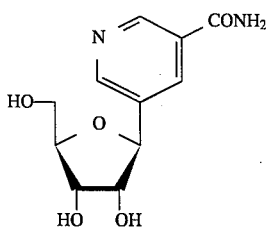

which is isosteric to nicotinamide riboside, was synthesized by these inventors [Kabat, Pankiewicz, Watanabe, *J. Med. Chem.*, 1987, 30, 924–927; Kabat et al., *Chem. Pharm. Bull.*, 1988, 36, 634–640; Pankiewicz et al., *J. Org. Chem.*, 1988, 53, 3473–3479] in the hope that such an analogue may be converted biologically into the corresponding nicotinamide adenine dinucleotide, NAD coenzyme, analog having the structure:

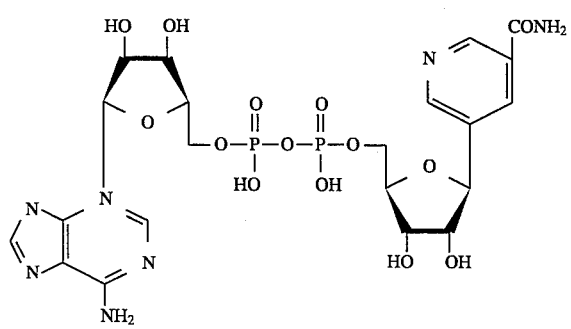

and exert biological activities. The non-charged NAD isostere (2), which is incapable of participating in biological oxidation-reduction process(es) may inhibit the NAD-dependent enzyme, IMP-dehydrogenase, and may induce anticancer activity by blocking the de novo GMP synthesis.

The NAD analog (2) which contains the C-nucleoside (1), was found to be a general competitive inhibitor (with respect to NAD) of various dehydrogenases such as inosine monophosphate dehydrogenase (IMPDH), glutamate dehydrogenase (GDH), lactate dehydrogenase (LDH) and malate dehydrogenase (MDH). Interestingly, the NAD analogue (2) exhibited highly potent and selective inhibitory activity against alcohol dehydrogenase from horse liver.

The present invention relates to the novel class of NAD analogs which contain the nicotinamide, picolinamide or isonicotinamide C-nucleoside in place of nicotinamide riboside. The compounds of this invention have the pyrophosphate (—P—O—P—) bridge connecting the nucleosides or, alternatively, can have a methylene diphosphonate (—P—CH$_2$—P—), or difluoromethylene diphosphonate (—P—CF$_2$—P—) group as the bridge.

Analogues that contain a methylene diphosphonate (—P—CH$_2$—P—) or difluoromethylene diphosphonate (—P—CF$_2$—P—) group in place of the pyrophosphate (—P—O—P—) bridge are resistant to enzymic hydrolysis to their corresponding nucleoside 5'-monophosphates. The 2'-fluoroinated adenosine analogues cannot be converted into the corresponding NADP analogues. Such analogues, therefore, cannot interfere with NADP dependent enzymes. In addition, fluorine substituted NAD analogues, as more lipophilic than their corresponding hydroxyl or pyrophosphate groups containing counterparts, could penetrate biological membranes and may better fit to the hydrophobic binding pocket of dehydrogenases.

The compositions of this invention are useful as potent inhibitors of various dehydrogenases of eucaryotic and procaryotic origin. These compounds may also be utilized as therapeutic agents exhibiting anticancer and antiviral activity.

SUMMARY OF THE INVENTION

This invention provides a compound having the structure:

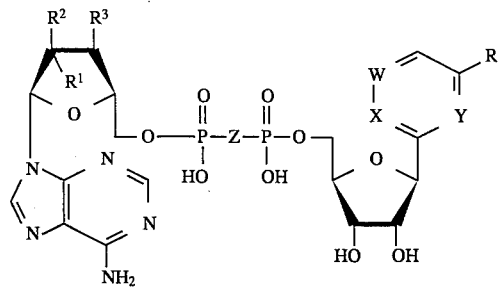

wherein $R^1$, $R^2$, and $R^3$ are same or different, and are hydrogen, hydroxyl, or fluorine; Z is O, CH$_2$ or CF$_2$; R is chlorine, bromine, iodine, carbonitrile, carboxylic ester, or carboxamide; and one of W, X and Y is N or N$^+$R', wherein R' is methyl or ethyl, and all others are CH; provided that $R^1$ is not H when $R^2$ and $R^3$ are OH, Z is O, R is carboxamide and W is N or N$^+$R'.

This invention also provides a compound having the structure:

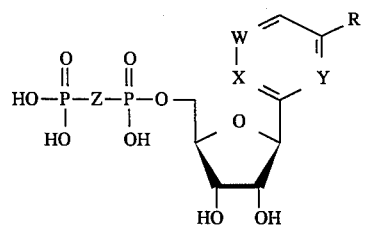

wherein Z is CH$_2$ or CF$_2$; R is chlorine, bromine, iodine, carbonitrile, carboxylic ester, or carboxamide; and one of W, X and Y is N or N$^{30}$ R', wherein R' is methyl or ethyl, and all others are CH.

This invention also provides a compound having the structure:

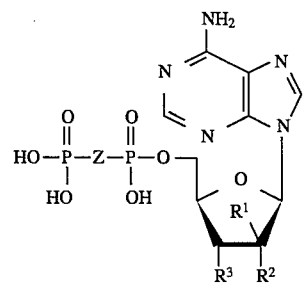

wherein Z is $CH_2$ or $CF_2$; and $R^1$, $R^2$, and $R^3$ are same or different, and are hydrogen, hydroxyl, or fluorine.

This invention also provides a pharmaceutical composition which comprises any of the above-identified compounds and a pharmaceutically acceptable carrier.

This invention further provides a method of treating a mammal having a NAD-dependent enzyme associated disorder which comprises administering to the mammal a pharmaceutically effective amount of a compound having the structure:

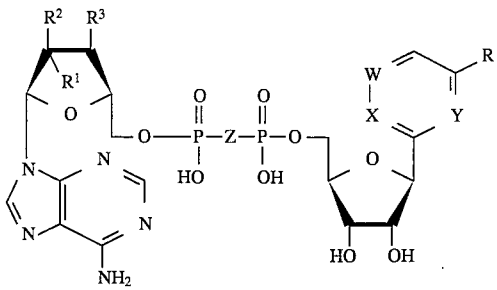

wherein $R^1$, $R^2$, and $R^3$ are same or different, and are hydrogen, hydroxyl, or fluorine; Z is O, $CH_2$ or $CF_2$; R is chlorine, bromine, iodine, carbonitrile, carboxylic ester, or carboxamide; and one of W, X and Y is N or $N^+R'$, wherein R' is methyl or ethyl, and all others are CH;

effective to inhibit the NAD-dependent enzyme, thereby treating the disorder.

Finally, this invention provides methods of preparing the above-identified compounds.

DETAILED DESCRIPTION

This invention provides a compound having the structure:

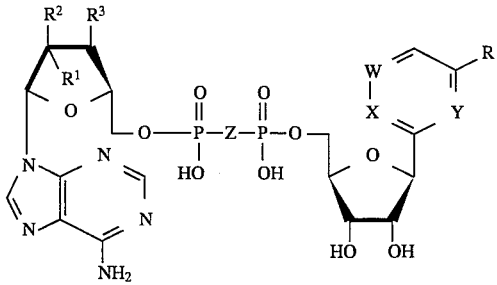

wherein $R^1$, $R^2$, and $R^3$ are same or different, and are hydrogen, hydroxyl, or fluorine; Z is O, $CH_2$ or $CF_2$; R is chlorine, bromine, iodine, carbonitrile, carboxylic ester, or carboxamide; and one of W, X and Y is N or $N^+R'$, wherein R' is methyl or ethyl, and all others are CH; provided that $R^1$ is not H when $R^2$ and $R^3$ are OH, Z is O, R is carboxamide and W is N or $N^+R'$.

Compounds having the above-identified structure, although not limited to the following compounds, may be selected from the group consisting of:

5-(β-D-Ribofuranosyl)3-carboxyamidopyridine-(5'-5")-adenosine pyrophosphate,
6-(β-D-Ribofuranosyl)2-carboxyamidopyridine-(5'-5")-adenosine pyrophosphate,
2-(β-D-Ribofuranosyl)4-carboxyamidopyridine-(5'-5")-adenosine pyrophosphate,
5-(β-D-Ribofuranosyl)-3-cyanopyridine-(5'-5")-adenosine pyrophosphate,
6-(β-D-Ribofuranosyl)-2-cyanopyridine-(5'-5")-adenosine pyrophosphate,
2-(β-D-Ribofuranosyl)-4-cyanopyridine-(5'-5")-adenosine pyrophosphate,
5-(β-D-Ribofuranosyl)3-carboxyamidopyridine-(5'-5")-2'-deoxyadenosine pyrophosphate,
6-(β-D-Ribofuranosyl)2carboxyamidopyridine-(5'-5")-2'-deoxyadenosine pyrophosphate,
2-(β-D-Ribofuranosyl)4-carboxyamidopyridine-(5'-5")-2'-deoxyadenosine pyrophosphate,
5-(β-D-Ribofuranosyl)-3-cyanopyridine-(5'-5")-2'-deoxyadenosine pyrophosphate,
6-(β-D-Ribofuranosyl)-2-cyanopyridine-(5'-5")-2'-deoxyadenosine pyrophosphate,
2-(β-D-Ribofuranosyl)-4-cyanopyridine-(5'-5")-2'-deoxyadenosine pyrophosphate,
5-(β-D-Ribofuranosyl)3-carboxyamidopyridine-(5'-5")-2'-deoxy-2'-fluoroadenosine pyrophosphate,
6-(β-D-Ribfuranosyl)2-carboxyamidopyridine-(5'-5")-2"-deoxy-2"-fluoroadenosine pyrophosphate,
2-(β-D-Ribofuranosyl)4-carboxyamidopyridine-(5'-5")-2'-deoxy-2'-fluoroadenosine pyrophosphate,
5-(β-D-Ribofuranosyl)-3-cyanopyridine-(5'-5")-2'-deoxy-2'-fluoroadenosine pyrophosphate,
6-(β-D-Ribofuranosyl)-2-cyanopyridine-(5'-5")-2'-deoxy-2'-fluoroadenosine pyrophosphate,
2-(β-D-Ribofuranosyl)-4-cyanopyridine-(5'-5")-2'-deoxy-2'-fluoroadenosine pyrophosphate,
5-(β-D-Ribofuranosyl)3-carboxyamidopyridine-(5'-5")-3'-deoxy-3'-fluoroadenosine pyrophosphate,
6-(β-D-Ribofuranosyl)picolinamide-(5'-5")-3'-deoxy-3'-fluoroadenosine pyrophosphate,
2-(β-D-Ribofuranosyl)isonicotinamide-(5'-5")-3'-deoxy-3'-fluoroadenosine pyrophosphate,
5-(β-D-Ribofuranosyl)-3-cyanopyridine-(5'-5")-3'-deoxy-3'-fluoroadenosine pyrophosphate,
6-(β-D-Ribofuranosyl)-2-cyanopyridine-(5'-5")-3'-deoxy-3'-fluoroadenosine pyrophosphate,
2-(β-D-Ribofuranosyl)-4-cyanopyridine-(5'-5")-3'-deoxy-3'-fluoroadenosine pyrophosphate,
5-(β-D-Ribofuranosyl)3-carboxyamidopyridine-(5'-5")-9-(2'-deoxy-2'-fluoro-β-D-arabinofuranosyl)-adenine pyrophosphate,
6-(β-D-Ribofuranosyl)picolinamide-(5'-5")-9-(2'deoxy-2'-deoxy-2'-fluoro-β-D-arabinofuranosyl)-adenine pyrophosphate,
2-(β-D-Ribofuranosyl)isonicotinamide-(5'-5")-9-(2'-deoxy-2'-fluoro-β-D-arabinofuranosyl)-adenine pyrophosphate,
5-(β-D-Ribofuranosyl)-3-cyanopyridine-(5'-5")-9-(2'-deoxy-2'-fluoro-β-D-arabinofuranosyl)-adenine pyrophosphate,
6-(β-D-Ribofuranosyl)-2-cyanopyridine-(5'-5")-9-(2'-deoxy-2'-fluoro-β-D-arabinofuranosyl)-adenine pyrophosphate,
2-(β-D-Ribofuranosyl)-4-cyanopyridine-(5'-5")-9-(2'-deoxy-2'-fluoro-β-D-arabinofuranoyl)-adenine pyrophosphate,
$P^1$-[5-(β-D-Ribofuranosyl)3-carboxyamidopyridine-5'-yl]-$P^2$-[adenosine-5"-yl]methylenediposphonate,
$P^1$-[6-(β-D-Ribofuranosyl)2-carboxyamidopyridine-5'-yl]-$P^2$-[adenosine -5"-yl]methylenediphosphonate,
$P^1$-[2-(β-D-Ribofuranosyl)4-carboxyamidopyridine-5'-yl]-$P^2$-[adenosine-5"-yl]methylenediphosphonate,
$P^1$-[5-(β-D-Ribofuranosyl)-3-cyanopyridine-5'-yl]-$P^2$-[adenosine-5"-yl]methylenediphosphonate,
$P^1$-[6-(β-D-Ribofuranosyl)-2-cyanopyridine-5'-yl]-$P^2$-[adenosine-5"-yl]methylenediphosphonate,
$P^1$-[2-(β-D-Ribofuranosyl)-4-cyanopyridine-5'-yl]-$P^2$-[adenosine-5"-yl]methylenediphosphonate,
$P^1$-[5-(β-D-Ribofuranosyl)3-carboxyamidopyridine-5'-yl]-$P^2$-[2'-deoxyadenosine-5"-yl]methylenediphosphonate,
$P^1$-[6-(β-D-Ribofuranosyl)2-carboxyamidopyridine-5'-yl]-$P^2$-[2'-deoxyadenosine-5"-yl]methylenediphosphonate, $P^1$-[2-(β-D-Ribofuranosyl)4-carboxyamidopyridine-5'-yl]-$P^2$-[2'-deoxyadenosine-5"-yl]methylenediphosphonate,
$P^1$-[5-(β-D-Ribofuranosyl)-3-cyanopyridine-5'-yl]$P^2$-[2'-deoxyadenosine-5"-yl]methylenediphosphonate,
$P^1$-[6-(β-D-Ribofuranosyl)-2-cyanopyridine-5'-yl]-$P^2$-2'-deoxyadenosine-5"-yl]methylenediphosphonate,
$P^1$-[2-(β-D-Ribofuranosyl)-4-cyanopyridine-5'-yl]-$P^2$-[2'-deoxyadenosine-5"-yl]methylenediphosphonate,
$P^1$-[5-(β-D-Ribofuranosyl)3-carboxyamidopyridine-5'-yl]-$P^2$-[2'-deoxy-2'-fluoroadenosine-5"-yl]methylenediphosphonate,
$P^1$-[6-(β-D-Ribofuranosyl)2-carboxyamidopyridine-5'-yl]-$P^2$-[2'-deoxy-2'-fluoroadenosine-5"-yl]methylenediphosphonate,
$P^1$-[2-(β-D-Ribofuranosyl)4-carboxyamidopyridine-5'-yl]-$P^2$-[2'-deoxy-2'-fluoroadenosine-5"-yl]methylenediphosphonate,
$P^1$-[5-(β-D-Ribofuranosyl)-3-cyanopyridine-5'-yl]-$P^2$-[2'-deoxy-2'-fluoroadenosine-5"-yl]methylenediphosphonate,
$P^1$-[6-(β-D-Ribofuranosyl)-2-cyanopyridine-5'-yl]-$P^2$-[2'-deoxy-2'-fluoroadenosine-5"-yl]methylenediphosphonate,
$P^1$-[2-(β-D-Ribofuranosyl)-4-cyanopyridine-5'-yl]-$P^2$-[2'-deoxy-2'-fluoroadenosine-5"-yl]methylenediphosphonate,
$P^1$-[5-(β-D-Ribofuranosyl)3-carboxyamidopyridine-5'-yl]-$P^2$-[3'-deoxy-3'-fluoroadenosine-5"-yl]-methylenediphosphonate,
$P^1$-[6-(β-D-Ribofuranosyl)2-carboxyamidopyridine-5'-yl]-$P^2$-[3'-deoxy-3'-fluoroadenosine-5"-yl]methylenediphosphonate,
$P^1$-[2-(β-D-Ribofuranosyl)4-carboxyamidopyridine-5'-yl]-$P^2$-[3'-deoxy-3'-fluoroadenosine-5"-yl]methylenediphosphonate,
$P^1$-[5-(β-D-Ribofuranosyl)-3-cyanopyridine-5'-yl]-$P^2$-[3'-deoxy-3'-fluoroadenosine-5"-yl]methylenediphosphonate,
$P^1$-[6-(β-D-Ribofuranosyl)-2-cyanopyridine-5'-yl]-$P^2$-[3'-deoxy-3'-fluoroadenosine-5"-yl]methylenediphosphonate,
$P^1$-[2-(β-D-Ribofuranosyl)-4-cyanopyridine-5'-yl]-$P^2$-[3'-deoxy-3'-fluoroadenosine-5"-yl]methylenediphosphonate,
$P^1$-[5-(β-D-Ribofuranosyl)3-carboxyamidopyridine-5'-yl]-$P^2$-[9-(2'-deoxy-2'-fluoro-β-D-arabinofuranosyl)adenine-5"-yl]methylenediphosphonate,
$P^1$-[6-(β-D-Ribofuranosyl)2-carboxyamidopyridine-5'-yl]-$P^2$-[9-(2'-deoxy-2'-fluoro-β-D-arabinofuranosyl)adenine-5"-yl]methylenediphosphonate,
$P^1$-[2-(β-D-Ribofuranosyl)4-caboxyamidopyridine-5'-yl]-$P^2$-[9-(2'-deoxy-2'-fluoro-β-D-arabinofuranosyl)adenine-5"-yl]methylenediphosphonate,
$P^1$-[5-(β-D-Ribofuranosyl)-3-cyanopyridine-5'-yl]-$P^2$-[9-(2'-deoxy-2'-fluoro-β-D-arabinofuranosyl)adenine-5"-yl]methylenediphosphonate,
$P^1$-[6-(β-D-Ribofuranosyl)-2-cyanopyridine-5'-yl]-$P^2$-[9-(2'-deoxy-2'-fluoro-β-D-arabinofuranosyl)adenine-5"-yl]methylenediphosphonate,
$P^1$-[2-(β-D-Ribofuranosyl)-4-cyanopyridine-5'-yl]-$P^2$-[9-(2'-deoxy-2'-fluoro-β-D-arabinofuranosyl)-adenine-5"-yl]methylenediphosphonate,
$P^1$-[5-(β-D-Ribofuranosyl)3-carboxyamidopyridine-5'-yl]-$P^2$-[adenosine-5"-yl]difluoromethylenediphosphonate,
$P^1$-[6-(β-D-Ribofuranosyl)2-carboxyamidopyridine-5'-yl]-$P^2$-[adenosine-5"-yl]difluoromethylenediphosphonate,
$P^1$-[2-(β-D-Ribofuranosyl)4-carboxyamidopyridine-5'-yl]-$P^2$-[adenosine-5"-yl]difluoromethylenediphosphonate,
$P^1$-[5-(β-D-Ribofuranosyl)-3-cyanopyridine-5'-yl]-$P^2$-[adenosine-5"-yl]difluoromethylenediphosphonate,
$P^1$-[6-(β-D-Ribofuranosyl)-2-cyanopyridine-5'-yl]-$P^2$-[adenosine-5"-yl]difluoromethylenediphosphonate,
$P^1$-[2-(β-D-Ribofuranosyl)-4-cyanopyridine-5'-yl]-$P^2$-[adenosine-5"-yl]difluoromethylenediphosphonate,
$P^1$-[5-(β-D-Ribofuranosyl)3-carboxyamidopyridine-5'-yl]-$P^2$-[2'-deoxyadenosine-5"-yl]difluoromethylenediphosphonate,
$P^1$-[6-(β-D-Ribofuranosyl)2-carboxyamidopyridine-5'-yl]-$P^2$-[2'-deoxyadenosine-5"-yl]difluoromethylenediphosphonate,
$P^1$-[2-(β-D-Ribofuranosyl)4-carboxyamidopyridine-5'-yl]-$P^2$-[2'-deoxyadenosine-5"-yl]difluoromethylenediphosphonate,
$P^1$-[5-(β-D-Ribofuranosyl)-3-cyanopyridine-5'-yl]-$P^2$-[2'-deoxyadenosine-5"-yl]difluoromethylenediphosphonate,
$P^1$-[6-(β-D-Ribofuranosyl)-2-cyanopyridine-5'-yl]-$P^2$-2'-deoxyadenosine-5"-yl]difluoromethylenediphosphonate,
$P^1$-[2-(β-D-Ribofuranosyl)-4-cyanopyridine-5'-yl]-$P^2$-[2'-deoxyadenosine-5"-yl]difluoromethylenediphosphonate,
$P^1$-[5-(β-D-Ribofuranosyl)3-carboxyamidopyridine-5'-yl]-$P^2$-[2'-deoxy-2'-fluoroadenosine-5"-yl]difluoromethylenediphosphonate,
$P^1$-[6-(β-D-Ribofuranosyl)2-carboxyamidopyridine-5'-yl]-$P^2$-[2'-deoxy-2'-fluoroadenosine-5"-yl]difluoromethylenediphosphonate,
$P^1$-[2-(β-D-Ribofuranosyl)4-carboxyamidopyridine-5'-yl]-$P^2$-[2'-deoxy-2'-fluoroadenosine-5"-yl]difluoromethylenediphosphonate,
$P^1$-[5-(β-D-Ribofuranosyl)-3-cyanopyridine-5'-yl]-$P^2$-[2'-deoxy-2'-fluoroadenosine-5"-yl]difluoromethylenediphosphonate,
$P^1$-[6-(β-D-Ribofuranosyl)-2-cyanopyridine-5'-yl]-$P^2$-[2'-deoxy-2'-fluoroadenosine-5"-yl]difluoromethylenediphosphonate,
$P^1$-[2-(β-D-Ribofuranosyl)-4-cyanopyridine-5'-yl]-$P^2$-[2'-deoxy-2'-fluoroadenosine-5"-yl]difluoromethylenediphosphonate,
$P^1$-[5-(β-D-Ribofuranosyl)3-carboxyamidopyridine-5'-yl]-$P^2$-[3'-deoxy-3'-fluoroadenosine-5"-yl]-difluoromethylenediphosphonate,
$P^1$-[6-(β-D-Ribofuranosyl)2-carboxyamidopyridine-5'-yl]-$P^2$-[3'-deoxy-3'-fluoroadenosine-5"-yl]-difluoromethylenediphosphonate,
$P^1$-(2-β-D-Ribofuranosyl)4-carboxyamidopyridine-5'-yl-$P^2$-3'-deoxy-3'-fluoroadenosine-5"-yl]-difluoromethylenediphosphonate,
$P^1$-[5-(β-D-Ribofuranosyl)-3-cyanopyridine-5'-yl]-$P^2$-[3'-deoxy-3'-fluoroadenosine-5"-yl]-difluoromethylenediphosphonate,
$P^1$-[6-(β-D-Ribofuranosyl)-2-cyanopyridine-5'-yl]-$P^2$-[3'-deoxy-3'-fluoroadenosine-5"-yl]-difluoromethylenediphosphonate,
$P^1$-[2-(β-D-Ribofuranosyl)-4-cyanopyridine-5'-yl]-$P^2$-[3'-deoxy-3'-fluoroadenosine-5"-yl]-difluoromethylenediphosphonate,
$P^1$-[5-(β-D-Ribofuranosyl)3-carboxyamidopyridine-5'-yl]-$P^2$-[9-(2'-deoxy-2'-fluoro-β-D-arabino-furanosyl)]adenine-5"-yl]-difluoromethylenediphosphonate,
$P^1$-[6-(β-D-Ribofuranosyl)2-carboxyamidopyridine-5'-yl]-$P^2$-[9-(2'-deoxy-2'-fluoro-β-D-arabino-furanosyl)]adenine-5"-yl]-difluoromethylenediphosphonate,
$P^1$-[2-(β-D-Ribofuranosyl)4-carboxyamidopyridine-5'-yl]-$P^2$-[9-(2'-deoxy-2'fluoro-β-D-arabino-furanosyl)-adenine-5"-yl]-difluoromethylenediphosphonate,
$P^1$-[5-(β-D-Ribofuranosyl)-3-cyanopyridine-5'-yl]-$P^2$-[9-(2'-deoxy-2'-fluoro-β-D-arabino-furanosyl)-adenine-5"-yl]-difluoromethylenediphosphonate,
$P^1$-[6-(β-D-Ribofuranosyl)-2-cyanopyridine-5'-yl]-$P^2$-[9-(2'-deoxy-2'-fluoro-β-D-arabino-furanosyl)-adenine-5"-yl]-difluoromethylenediphosphonate, and
$P^1$-[2-(β-D-Ribofuranosyl)-4-cyanopyridine-5'-yl]-$P^2$-[9-(2'-deoxy-2'-fluoro-β-D-arabino-furanosyl)-adenine-5"-yl]-difluoromethylenediphosphonate.

This invention also provides a compound having the structure:

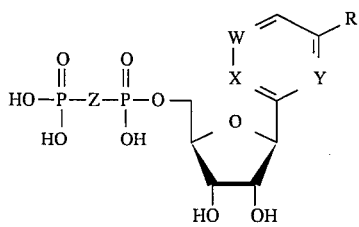

wherein $Z$ is $CH_2$ or $CF_2$; R is chlorine, bromine, iodine, carbonitrile, carboxylic ester, or carboxamide; and one of W, X and Y is N or $N^+R'$, wherein R' is methyl or ethyl, and all others are CH.

Compounds having the above-identified structure, although not limited to the following compounds, may be selected from the group consisting of:
(5-β-D-Ribofuranosyl3-carboxyamidopyridine-5'-yl)methylenediphosphonate
(6-β-D-Ribofuranosyl2-carboxyamidopyridine-5'-yl)methylenediphosphonate,
(2-β-D-Ribofuranosyl4-carboxyamidopyridine-5'-yl)methylenediphosphonate,
(5-β-D-Ribofuranosyl-3-cyanopyridine-5'-yl)methylenediphosphonate,
(6-β-D-Ribofuranosyl-2-cyanopyridine-5'-yl)methylenediphosphonate,
(2-(β-D-Ribofuranosyl-4-cyanopyridine-5'-yl)methylenediphosphonate,
(5-β-D-Ribofuranosyl3-carboxyamidopyridine-5'-yl)difluoromethylene-diphosphonate,
(6-β-D-Ribofuranosyl2-carboxyamidopyridine-5'-yl)difluoromethylene-diphosphonate,
(2-β-D-Ribofuranosyl4-carboxyamidopyridine-5'-yl)difluoromethylene-diphosphonate,
(5-β-D-Ribofuranosyl-3-cyanopyridine-5'-yl)difluoromethylene-diphosphonate,
(6-β-D-Ribofuranosyl-2-cyanopyridine-5'-yl)difluoromethylene-diphosphonate, and
(2-(β-D-Ribofuranosyl-4-cyanopyridine-5'-yl)difluoromethylene-diphosphonate.

This invention also provides a compound having the structure:

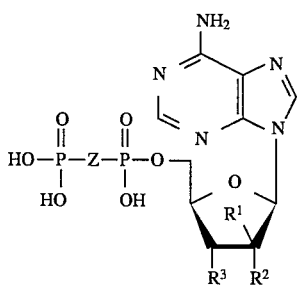

wherein $Z$ is $CH_2$ or $CF_2$; and $R^1$, $R^2$, and $R^3$ are same or different, and are hydrogen, hydroxyl, or fluorine.

Compounds having the above-identified structure, although not limited to the following compounds, may be selected from the group consisting of:
(Adenosin-5'-yl)methylenediphosphonate,
(2'-deoxyadenosin-5'-yl)methylenediphosphonate,
(2'-deoxy-2'-fluoroadenosin-5'-yl)methylenediphosphonate,
(3'-deoxy-3'-fluoroadenosin-5'-yl)methylenediphosphonate,
[9-(2'-deoxy-2'-fluoro-β-D-arabinofuranosyl)adenine-5'-yl] methylenediphosphonate,
(Adenosin-5'-yl)difluoromethylenediphosphonate,
(2'-deoxyadenosin-5'-yl)difluoromethylenediphosphonate,
(2'-deoxy-2'-fluoroadenosin-5'-yl)difluoromethylenediphosphonate,
(3'-deoxy-3'-fluoroadenosin-5'-yl)difluoromethylenediphosphonate, and
[9-(2'-deoxy-2'-fluoro-β-D-arabinofuranosyl)adenine-5'-yl] difluoromethylenediphosphonate.

This invention further provides a method of treating a mammal having a NAD-dependent enzyme associated disorder which comprises administering to the mammal a pharmaceutically effective amount of a compound having the structure:

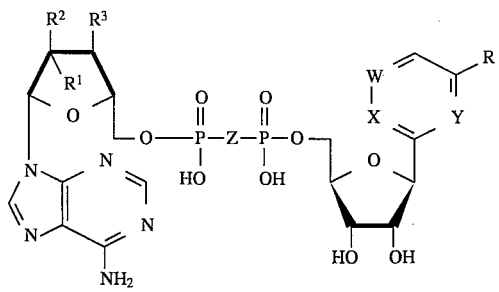

wherein $R^1$, $R^2$, and $R^3$ are same or different, and are hydrogen, hydroxyl, or fluorine; Z is O, $CH_2$ or $CF_2$; R is chlorine, bromine, iodine, carbonitrile, carboxylic ester, or carboxamide; and one of W, X and Y is N or $N^+R'$, wherein R' is methyl or ethyl, and all others are CH;

effective to inhibit the NAD-dependent enzyme, thereby treating the disorder.

For the purpose of this invention, the term "NAD-dependent enzyme" means an enzyme which requires the presence of the co-enzyme NAD in order to assist the enzymatic reaction. Examples of enzymes which are dependent on NAD are known to those skilled in the art and include, but are not limited to, malate dehydrogenase, lactate dehydrogenase, alcohol dehydrogenase, inosine monophosphat dehydrogenase, glutamate dehydrogenase, isocitrate dehydrogenase, 6-phosphogluconate dehydrogenase, aldehyde dehydrogenase, dihydrosteroid dehydrogenase and dihydrofolate reductase.

For the purposes of this invention, the term "NAD-dependent enzyme associated disorder" is any disorder which arises or is aggrivated due to the enzymatic action of an NAD-dependent enzyme. Examples of such disorders are readily determinable by those skilled in the art.

In a preferred embodiment of this invention the NAD-dependent enzyme is alcohol dehydrogenase. In a second preferred embodiment of this invention the NAD-dependent enzyme is inosine monophosphate dehydrogenase.

Examples of disorders associated with the enzymatic action of alcohol dehydrogenase include, but are not limited to, acute alcohol posioning from the ingestion of such substances as ethanol, methanol or isopropyl alcohol, ethylene glycol intoxication, ethanol-induced hypoglycemia and lactacidemia.

Examples of disorders associated with the enzymatic action of inosine monophosphate dehydrogenase include, but are not limited to disorders characterized by the proliferation of malignant cells. Examples of disorders which are associated with the proliferation of malignant cells to which the compounds of the subject invention would be effective are readily determinable by those skilled in the art and include, but are not limited to, cancers of the breast, colon, stomach, pancreas, ovary, head and neck, and urinary bladder, leukemias such as acute lymphocytic, acute granulocytic and chronic granulocytic leukemias, hairy cell leukemia, chronic lymphocytic leukemia, and other malignant disorders such as mycosis fungoides.

This invention also provides a pharmaceutical composition which comprises any of the above-identified compounds and a pharmaceutically acceptable carrier. In the preferred embodiment of this invention, the compounds are administered to the mammal as a pharmaceutical composition.

As used herein, the term "pharmceutically acceptable carrier" encompasses any of the standard pharmaceutical carriers such as an organic or inorganic inert carrier material suitable for enteral or parenteral administration which include, but are not limited to, water, gelatin, gum arabic, lactose, starches, magnesium stearate, talc, vegetable oils, polyalkylene glycols, petroleum gelly, etc. The pharmacological preparations can be made up in solid form such as tablets, dragees, suppositories or capsules, or in liquid form such as solutions, suspensions, or emulsions. The preparations may be sterilized and/or contain adjuvants such as preserving, stabilizing, wetting or emulsifying agents, salts for varying the osmotic pressure, or buffers. Such preparations may also contain other therapeutic agents.

For the purposes of this invention, the term "pharmaceutically effective amount" of the compound means any amount of the compound which, when incorporated in the pharmaceutical composition, will be effective to inhibit the enzymatic action of an NAD-dependent enzyme and, thereby, treat an NAD-dependent enzyme associated disorder but less than an amount which would be toxic to the mammal. In the practice of this invention the amount of the compound incorporated in the pharmaceutical composition may vary widely. Factors considered when determining the precise amount are well known to those skilled in the art. Examples of such factors include, but are not limited to, the subject being treated, the specific pharmaceutical carrier and route of administration being employed and the frequency with which the composition is to be administered. In a preferred embodiment of this invention, the pharmaceutically effective amount of the compound is in the range of 10 picomolar to 10 milimolar. In a particularly preferred embodiment the pharmaceutically effective amount is in the range of 10 micromolar.

In the practice of this invention, the administration of the composition may be effected by any of the well known methods including, but not limited to, oral, intravenous, intraperitoneal, intramuscular or subcutaneous or topical administration.

The compounds of this invention are prepared according to the following methods.

In the first method, the nucleosides are converted to their corresponding 5'-monophosphates and then coupled together to form the dinucleotides of this invention as follows:

(a) reacting a compound having the structure:

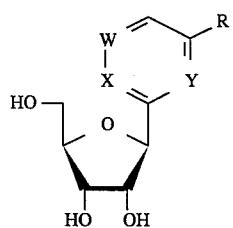

Formula II wherein R is chlorine, bromine, iodine, carbonitrile, carboxylic ester, or carboxamide; and one of W, X and Y is N or N⁺R', wherein R' is methyl or ethyl, and all others are CH;

with phosphorous oxychloride in triethylphosphate under suitable conditions to form the nucleoside 5'-monophosphate derivative of the compound;

(b) reacting a compound having the structure:

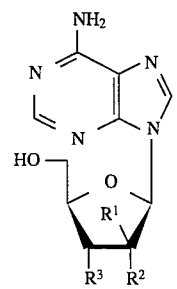

Formula III wherein R¹, R², and R³ are same or different, and are hydrogen, hydroxyl, or fluorine;

with phosphorous oxychloride in triethylphosphate under suitable conditions to form the nucleoside 5'-monophosphate derivative of the compound; and (c) reacting the 5'-monophosphate derivative formed in step (a) or (b) with carbonyldiimidazole or dicyclohexyl carbodiimide under suitable conditions to activate the 5'-monophosphate derivative and then contacting the activated compound with an unactivated compound of step (b) or (a), respectively, to form a compound having the structure:

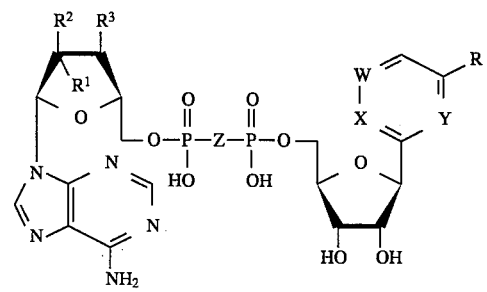

wherein R¹, R², and R³ are same or different, and are hydrogen, hydroxyl, or fluorine; Z is O; R is chlorine, bromine, iodine, carbonitrile, carboxylic ester, or carboxamide; and one of W, X and Y is N or N⁺R', wherein R' is methyl or ethyl, and all others are CH;

This method proceeds along the lines of known methods for the formation of the 5'-monophosphate derivatives of nucleosides; Yoshikawa et al., *Tetrahedron Letters*, 1967, 19, 5065–5068.

The dinucleotides of this invention, wherein Z is CH₂ or CF₂, can also be prepared by first forming the 5'-methylenediphosphonate or 5'-difluoromethylenediphosphonate derivative nucleosides of this invention and then coupling the derivatives to the corresponding nucleosides bearing the 5'-hydroxy group. The method proceeds as follows:

(a) reacting a compound having the structure:

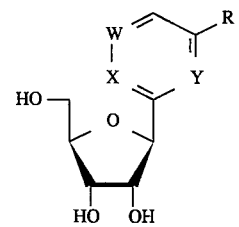

wherein R is chlorine, bromine, iodine, carbonitrile, carboxylic ester, or carboxamide; and one of W, X and Y is N or N⁺R', wherein R' is methyl or ethyl, and all others are CH;

with the precursor of a suitable protecting group under suitable conditions to form the 2'3'-O-protected nucleoside;

and (b) reacting the compound formed in step (a) with methylenediphosphonate tetrachloride in triethylphosphate under suitable conditions to form the 5'-methylenediphosphonate derivative, which, after reacting under suitable conditions to selectively remove the 2',3'-O-protecting groups, has the structure:

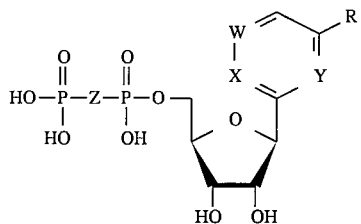

wherein Z is CH$_2$; R is chlorine, bromine, iodine, carbonitrile, carboxylic ester, or carboxamide; and one of W, X and Y is N or N$^+$R', wherein R' is methyl or ethyl, and all others are CH.

The dinucleotides of the invention are then prepared by reacting the 5'-methylenediphosphonate derivative formed above with the nucleoside having the structure:

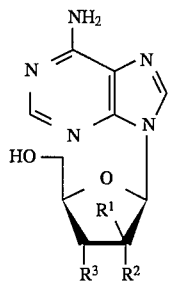

wherein R$^1$, R$^2$, and R$^3$ are same or different, and are hydrogen, hydroxyl, or fluorine;

under suitable conditions to allow for the coupling of the nucleosides to form the compound having the structure:

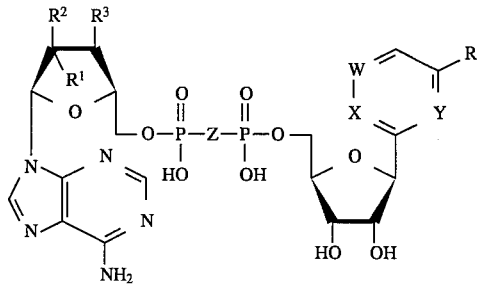

wherein Z is CH$_2$; R is chlorine, bromine, iodine, carbonitrile, carboxylic ester, or carboxamide; R$^1$, R$^2$, and R$^3$ are same or different, and are hydrogen, hydroxyl, or fluorine; and one of W, X and Y is N or N$^+$R', wherein R' is methyl or ethyl, and all others are CH.

The 5'-methylenediphosphonate derivative of the compound having the structure:

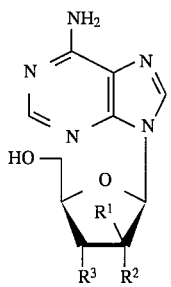

wherein R$^1$, R$^2$, and R$^3$ are same or different, and are hydrogen, hydroxyl, or fluorine;

is formed by the same method as above, wherein step (a) and the deprotection in step (b) are necessary only if any of R$^1$, R$^2$, and R$^3$ are hydroxyl groups.

The dinucleotides of the invention are then prepared by reacting the 5'-methylenediphosphonate derivative formed above with the nucleoside having the structure:

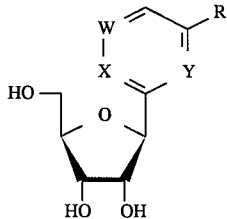

wherein R is chlorine, bromine, iodine, carbonitrile, carboxylic ester, or carboxamide; and one of W, X and Y is N or N$^+$R', wherein R' is methyl or ethyl, and all others are CH;

under suitable conditions to allow for the coupling of the nucleosides to form the compound having the structure:

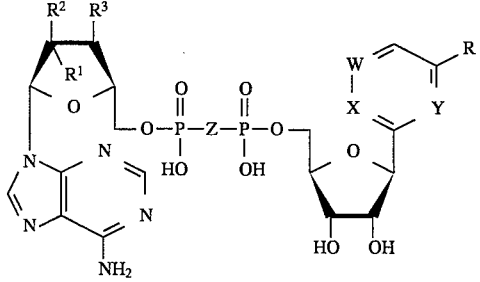

wherein Z is CH$_2$; R is chlorine, bromine, iodine, carbonitrile, carboxylic ester, or carboxamide; R$^1$, R$^2$, and R$^3$ are same or different, and are hydrogen, hydroxyl, or fluorine; and one of W, X and Y is N or N$^+$R', wherein R' is methyl or ethyl, and all others are CH.

In this method the reaction of step (a) comprises the selective protection of the vicinal cis hydroxy groups on the nucleoside to leave the 5'hydroxyl group as the remaining reactive site. For the purpose of this invention, a "precursor of a suitable protecting group" will comprise any compound that can be reacted with the compound of step (a) to allow for selective replacement of the vicinal hydroxyl cis hydroxy group with the corresponding O-protecting group. Examples of these are well known to those skilled in the art and include, but are not limited to, such compounds as isopropylidene and ethyl orthoformate. In this step the molar ratio of the reactants is in the range of 1:10 to 1:100 and the reaction is carried out at a temperature range of 0° C. to 50° C. for a period of 5 minutes to 2 days.

The reaction of step (b) comprises the formation of the 5'-methylenediphosphonate derivatives by reacting the compound formed in step (a) with methylenediphosphonate tetrachloride in triethylphosphate. In this step the molar ratio of the reactants is in the range of 2:1 to 1:10 and the reaction is carried out at a temperature range of −20° C. to 50° C. for a period of 5 minutes to 10 hours. Step (b) also comprises the selective removal of any protecting groups to form the 2',3'-hydroxy group substituents. The conditions of this step comprise acidic hydrolysis using Dowex 50 (H⁺), organic acid such as acetic acid, trifluoroacetic acid an the like, or inorganic acid such as hydrochloric acid, sulfuric acid and the like.

The coupling of the nucleosides is then carried out using coupling agents such as DCC (dicyclohexylcarbodiimide).

This invention also provides another method of making the dinucleotides of this invention wherein Z is CH2 or CF2 which proceeds as follows:

a) reacting a compound having the structure:

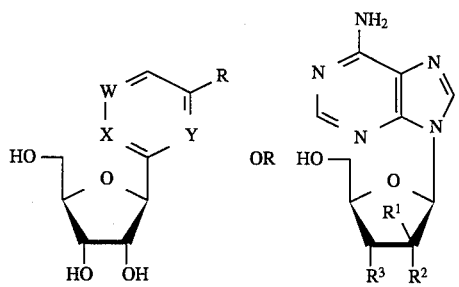

wherein R, $R^1$, $R^2$, $R^3$, W, X and Y are the same as defined previously;

with the precursor of a suitable protecting group to under suitable conditions to selectively protect the 2' and 3' hydroxyl groups on the compounds;

b) reacting the compounds formed in step (a) with tosyl chloride under tosylating conditions to form the compounds having the structure:

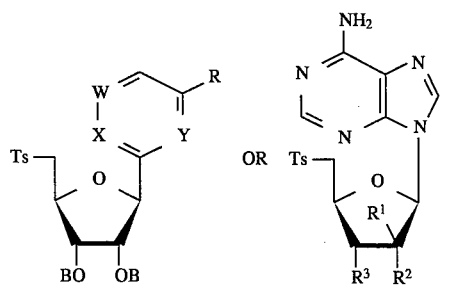

wherein Ts is tosyl and R, W, X and Y are the same as defined previously B is a protecting group and $R^1$, $R^2$, and $R^3$ are hydrogen, fluorine or an O-protecting group;

c) reacting the compound formed in step (b) with tris(tetra-n-butylammonium)methylene diphosphonate or tris(tetra-n-butylammonium)difluoromethylene diphosphonate in dimethylsulfoxide to form compounds having the structure:

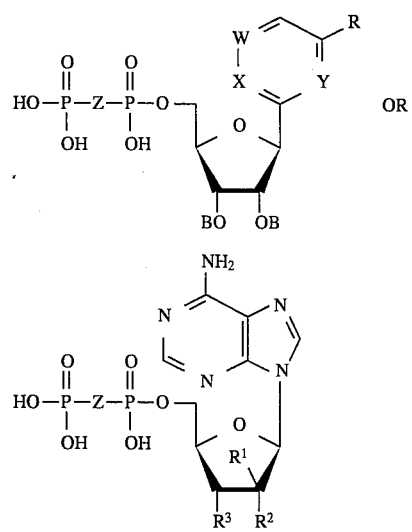

wherein Z is $CH_2$ or $CF_2$ and B, R, $R^1$, $R^2$, $R^3$, W, X and Y are the same as defined previously;

d) reacting the compound formed in step (c) with a compound having the structure:

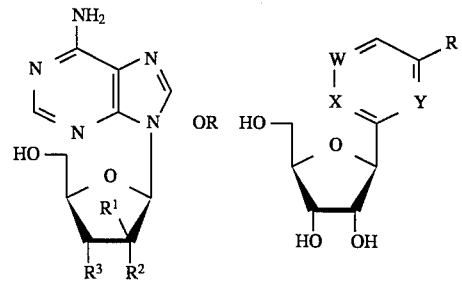

respectively, wherein R, W, X and Y are the same as defined previously and $R^1$, $R^2$, $R^3$ are hydrogen, hydroxy or fluorine;

under suitable conditions to form a compound having the structure:

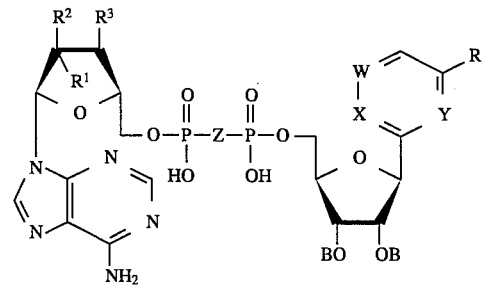

wherein Z is $CH_2$ or $CF_2$ and R, W, X and Y are the same as defined previously and $R^1$, $R^2$, $R^3$ are hydrogen, hydroxy, fluorine or O-protecting groups and B is H or a protecting group; and e) reacting the compound formed in step (d) under suitable conditions to selectively remove the protecting groups to form the compound having the structure:

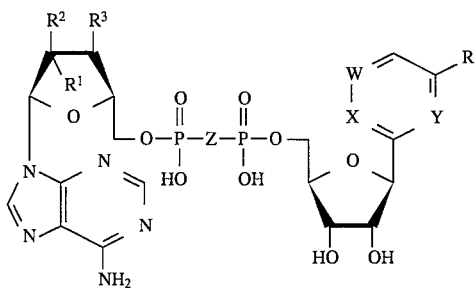

wherein Z is $CH_2$ or $CF_2$ and R, W, X and Y are the same as defined previously and $R^1$, $R^2$, $R^3$ are hydrogen, hydroxy or fluorine.

In this embodiment, the reaction of step (a) comprises the selective protection of the vicinal cis hydroxy groups on the nucleoside to leave the 5'hydroxyl group as the remaining reactive site. For the purpose of this invention, a "precursor of a suitable protecting group" will comprise any compound that can be reacted with the compound of step (a) to allow for selective replacement of the vicinal hydroxyl cis hydroxy group with the corresponding O-protecting group. Examples of these are well known to those skilled in the art and include, but are not limited to, such compounds as isopropylidene and ethyl orthoformate. In this step the molar ratio of the reactants is in the range of 1:1 to 1:100 and the reaction is carried out at a temperature range of 0° C. to 50° C. for a period of 5 minutes to 2 days.

The reaction of step (b) comprises the replacement of the 5'hydroxy group with a tosyl leaving group by reacting the compound formed in step (a) with tosyl chloride. In this step the molar ratio of the reactants is in the range of 1:1 to 1:10 and the reaction is carried out at a temperature range of –10° C. to 50° C. for a period of 5 minutes to 2 days.

The reaction of step (c) comprises the formation of the methylene- or difluoromethylene-diphosphonate derivative of the compound formed in step (b) by reacting the compound formed in step (b) with tris(tetra-n-butylammonium)methylene diphosphonate or tris(tetra-n-butylammonium)difluoromethylene diphosphonate, respectively, in dimethylsulfoxide. In this step the molar ratio of the reactants is in the range of 1:1 to 1:100 and the reaction is carried out at a temperature range of 0° C. to 50° C. for a period of 5 minutes to 10 days.

The reaction of step (d) comprises the coupling of the compound formed in step (c) with the corresponding nucleoside to form the dinucleotide complexes of this invention after deprotection in step (e). In step (d) the molar ratio of the reactants is in the range of 1:1 to 1:20 and the reaction is carried out at a temperature range of 0° C. to 50° C. for a period of 5 minutes to 10 days. In step (e), the deprotection of the compounds formed in step (d) is carried out at a temperature range of –20° C. to 50° C. for a period of 5 minutes to 1 day.

This invention is further illustrated in the Experimental Details section which follow. The Experimental Details section and Examples contained therein are set forth to aid in an understanding of the invention. This section is not intended to, and should not be interpreted to, limit in any way the invention set forth in the claims which follow thereafter.

Experimental Details

Preparation of the compounds

EXAMPLE 1

5-(β-D-Ribofuranosyl)3-carboxyamidopyridine-(5'-5")-adenosine pyrophosphate

To a suspension of 5-(β-D-ribofuranosyl)3-carboxyamidopyridine (100 mg, 0.4 mmol) in triethylphosphate (0.4 mL) is added phosphoryl chloride (72 mg, 0.48 mmol) at 0° C., and the mixture is stirred at room temperature for 4 hours. The reaction is quenched by addition of water (5 mL), and the mixture is neutralized with concentrated ammonia. The crude product is purified on a column of DEAE Sephadex A-25 (bicarbonate form) with 0.1M tetraethylammonium bicarbonate and then on a Dowex 50W-X8 ($H^+$) column to give the desired nucleoside 5'-monophosphate (76 mg). This compound is dried by coevaporation with pyridine (3×5 mL) and dimethylformamide (3×5 mL), and the residue is dissolved in dimethylformamide (0.7 mL). Carbonyldiimidazole (186 mg, 1.15 mmol) is added, and the progress of reaction was followed by thin layer chromatography (iPrOH-conc.$NH_4OH$—$H_2O$, 6;3;1, v/v/v). The excess of carbonyldiimidazole is hydrolyzed by addition of methanol (76 μL), and a solution of adenosine 5'-monophosphate (126 mg, 0.35 mmol) in dimethylformamide (4.4 mL) containing tributylamine (80 uL, 0.35 mmol) is added. The reaction mixture is stirred for 3 days. Water (10 mL) is added, and the mixture is concentrated in vacuo. The gummy residue is dissolved in water (40 mL) containing sodium acetate (60 mg) and extracted with chloroform (2×40 mL) and diethyl ether (2×40 mL). The aqueous layer is treated with triethylamine (60 mL, pH=10) and then lyophilized. The residue is purified on preparative cellulose plate using iPrOH-conc.$NH_4OH$—$H_2O$ (6:3:1), and then by a column of Dowex 50W-X8 ($H^+$) to give the desired pyrophosphate (90 mg, 60%) as a white powder. $^1$N NMR ($D_2O$) δ4.11–4.41 (m, 8H, H3', H3", H4',H4", H5',H5', H5", H5"), 4.54 (ψt, 1H, H2'), 4.76 (ψt, 1H, H2"), 5.06 (d, 1H, H1', $J_{1',2'}$=7.2 Hz), 6.14 (d, 1H, H1", $J_{1",2"}$=5.2 Hz), 8.43, 8.62 (two 1H singlets, H2, H8), 8.95–9.19 (m, 5H, H2, H4, H6, $NH_2$). MS (FAB) m/e 662 (M-H)$^-$; 664 MH$^+$ By following the same procedure, but using the corresponding nucleoside of Formula II instead of 3-carboxyamidopyridine riboside, the following dinucleoside pyrophosphates are prepared:

6-(β-D-Ribofuranosyl)2-carboxyamidopyridine-(5'-5")-adenosine pyrophosphate,
2-(β-D-Ribofuranosyl)4-carboxyamidopyridine-(5'-5")-adenosine pyrophosphate,
5-(β-D-Ribofuranosyl)-3-cyanopyridine-(5'-5")-adenosine pyrophosphate,
6-(β-D-Ribofuranosyl)-2-cyanopyridine-(5'-5")-adenosine pyrophosphate, and
2-(β-D-Ribofuranosyl)-4-cyanopyridine-(5'-5")-adenosine pyrophosphate.

EXAMPLE 2

6-(β-D-Ribofuranosyl)-(5'-5")-2"-deoxy-2"-fluoroadenosine pyrophosphate (2)

To a suspension of 6-(β-D-ribofuranosyl)2-carboxyamidopyridine (0.195 mmol) in triethylphosphate (0.195 mL) is added phosphoryl chloride (36 mg, 0.24mmol) at 0° C., the mixture is stirred at room temperature 4 hours, and the diluted with water (5 mL). After addition of concentrated ammonia, the crude product is purified on a DEAE Sephadex A-25 column (bicarbonate form) with 0.1M tetraethylammonium bicarbonate and Dowex 50W-X8 ($H^+$ form) to give 5'-monophosphate in 60–70% yield. The compound is then converted into the dinucleotide in reaction with 2'-deoxy-2'-fluoroadenosine 5'-monophosphate as described above. $^1$H NMR ($D_2O$) δ4.15–4.45 (m, 8H, H2', H3', H4', H5', H5', H4", H5", H5"), 4.61 (ddd, 1H, H3", $J_{2",3"}$=4.4 Hz, $J_{3",4"}$=7.3 Hz, $J_{3",F}$=20.4 Hz), 5.20 (ddd, 1H, H2", $J_{1",2"}$=2.0 Hz, $J_{2",F}$=51.9 Hz), 6.25 (dd, 1H, H1", $J_{1",F}$=16.0 Hz), 7.61 (dd, H5, $J_{3,5}$=1.0 Hz, $J_{4,5}$=7.7 Hz), 7.73 (dd, 1H, H3, $J_{3,4}$=7.7 Hz), 7.84 (t, 1H, H4, $J_{3,4}$=$J_{4,5}$=7.7 Hz), 8.11, 8.27 (two 1H singlets, H2, H8), $^{31}$P NMR (D$_2$O) δ–10.6, δ–10.7; J$_{POP}$= 21.0 Hz. MS (FAB) m/e 662 (M-H)$^-$, 664 MH$^+$ By following the same procedure, but using the corresponding nucleoside of Formula III instead of adenosine, the following dinucleoside pyrophosphates are prepared:

5-(β-D-Ribofuranosyl)3-carboxyamidopyridine-(5'-5")-2'-deoxyadenosine pyrophosphate,
2-(β-D-Ribofuranosyl)4-carboxyamidopyridine-(5'-5")-2'-deoxyadenosine pyrophosphate,
5-(β-D-Ribofuranosyl)-3-cyanopyridine-(5'-5")-2'-deoxyadenosine pyrophosphate,
6-(β-D-Ribofuranosyl)-2-cyanopyridine-(5'-5")-2'-deoxyadenosine pyrophosphate,
2-(β-D-Ribofuranosyl)-4-cyanopyridine-(5'-5")-2'-deoxyadenosine pyrophosphate,
5-(β-D-Ribofuranosyl)3-carboxyamidopyridine-(5'-5")-2'-deoxy-2'-fluoroadenosine pyrophosphate,
2-(β-D-Ribofuranosyl)4-carboxyamidopyridine-(5'-5")-2'-deoxy-2'-fluoroadenosine pyrophosphate,
5-(β-D-Ribofuranosyl)-3-cyanopyridine-(5'-5")-2'-deoxy-2'-fluoroadenosine pyrophosphate,
6-(β-D-Ribofuranosyl)-2-cyanopyridine-(5'-5")-2'-deoxy-2'-fluoroadenosine pyrophosphate,
2-(β-D-Ribofuranosyl)-4-cyanopyridine-(5'-5")-2'-deoxy-2'-fluoroadenosine pyrophosphate,
6-(β-D-Ribofuranosyl)2-carboxyamidopyridine-(5'-5")-3'-deoxy-3'-fluoroadenosine pyrophosphate,
2-(β-D-Ribofuranosyl)4-carboxyamidopyridine-(5'-5")-3'-deoxy-3'-fluoroadenosine pyrophosphate,
5-(β-D-Ribofuranosyl)-3-cyanopyridine-(5'-5")-3'-deoxy-3'-fluoroadenosine pyrophosphate,
6-(β-D-Ribofuranosyl)-2-cyanopyridine-(5'-5")-3'-deoxy-3'-fluoroadenosine pyrophosphate,
2-(β-D-Ribofuranosyl)-4-cyanopyridine-(5'-5")-3'-deoxy-3'-fluoroadenosine pyrophosphate,
6-(β-D-Ribofuranosyl)2-carboxyamidopyridine-(5'-5")-9-(2'-deoxy-2'-fluoro-β-D-arabinofuranosyl)adenine pyrophosphate,
2-(β-D-Ribofuranosyl)4-carboxyamidopyridine-(5'-5")-9-(2'-deoxy-2'-fluoro-β-D-arabinofuranosyl)adenine pyrophosphate,
5-(β-D-Ribofuranosyl)-3-cyanopyridine-(5'-5")-9-(2'-deoxy-2'-fluoro-β-D-arabinofuranosyl)adenine pyrophosphate,
6-(β-D-Ribofuranosyl)-2-cyanopyridine-(5'-5")-9-(2'-deoxy-2'-fluoro-β-D-arabinofuranosyl)adenine pyrophosphate, and
2-(β-D-Ribofuranosyl)-4-cyanopyridine-(5'-5")-9-(2'-deoxy-2'-fluoro-β-D-arabinofuranosyl)adenine pyrophosphate.

EXAMPLE 3

(5-β-D-Ribofuranosyl3-carboxyamidopyridine-5'-yl)methylenediphosphonate

The 5-β-D-Ribofuranosyl3-carboxyamidopyridine (253 mg, 1 mmol) was dissolved in acetone (5 mL), 2,2-dimethoxypropane (1 mL) and p-toluenosulfonic acid (380, 2 mmol) was added and the mixture was stirred at room temperature for 5 h. The mixture was neutralized with NaHCO$_3$, filtered, and concentrated in vacuo. The residue was extracted with chloroform (3×5 mL), the organic solution was washed with water (2×3 mL) and concentrated in vacuo to give 2',3'-O-isopropylidene-5-β-D-ribofuranosylnicotinamide (290, 99%). $^1$H NMR (CDCl$_3$) δ1.32 (s, 3H, iPr), 1.58 (s, 3H, iPr), 3.72–3.95 (m, 2H, H5', H5"), 4.17–4.21 (m, 1H, H4'), 4.40–4.50 (m, 1H, H3'), 4.71–4.80 (m, 1H, H2'), 4.83 (d, 1H, H1', J$_{1',2'}$=5.3 Hz), 6.90 (brs, 1H, NH$_2$), 7.56 (brs, 1H, NH$_2$), 8.19 (s, 1H, H4), 8.60 (s, 1H, H6), 8.86 (s, 1H, H2) The 2',3'-O-isopropylidene-5-β-D-ribofuranosyl3-carboxyamidopyridine (290 mg, 0.99 mmol) was added into solution of methylene diphosphonate tetrachloride (250 mg, 1 mol) in triethylphospate (5 mL). The mixture was stirred at room temperature for 2 h, poured into ice water (10 mL), stirred for 30 min., and then whole mixture was extracted with ethyl acetate (3×10 mL). The pH of the water solution was adjusted to 2 with HCl, the mixture was kept standing for 2 h and concentrated. The residue was purified on preparative HPLC column (Dynamax-300A C18 83 243 C, rate flow 20 mL/min.) with 0.1M TEAB followed by linear gradient of 0.1 TEAB/ag. acetonitrile (70%) to give (5-β-D-ribofuranosyl3-carboxyamidopyridine-5'-yl)methylenediphosphonate (440 mg, 72%) as bis triethylammonium salt. $^1$H NMR (D$_2$O δ2.12 (t, 2H, CH$_2$, J$_{P,H}$=20 Hz), 4.05–4.40 (m, 4H, H3', H4', H5', H5"), 4.55 (pseudot, 1H, H2'), 4.79 (d, 1H, H1', J$_{1',2'}$=4.9 Hz), 8.40 (s, 1H, H4), 8.72 (s, 1H, H4), 8.91 (s, 1H, H2). $^{31}$P NMR (D$_2$O) δ11.5 (d, J$_{P,P}$=9.5 Hz), 22.8 (d).

By following the same procedure, but using the corresponding nucleoside of Formula II instead of 3-carboxyamidopyridine riboside, the following methylenediphosphonates are prepared:

(6-β-D-Ribofuranosyl2-carboxyamidopyridine-5'-yl)methylenediphosphonate,
(2-β-D-Ribofuranosyl4carboxyamidopyridine-5'-yl)methylenediphosphonate,
(5-β-D-Ribofuranosyl-3-cyanopyridine-5'-yl)methylenediphosphonate,
(6-β-D-Ribofuranosyl-2-cyanopyridine-5'-yl)methylenediphosphonate, and
(2-(β-D-Ribofuranosyl-4-cyanopyridine-5'-yl)methylenediphosphonate.

EXAMPLE 4

(Adenosin-5'-yl)methylenediphosphonate

The 2',3'-O-isopropylidene adenosine (307 mg, 1 mmol) was added into solution of methylene diphosphonate tetrachloride (250 mg, 1 mol) in triethylphosphate (5 mL). The mixture was stirred at room temperature for 2 h, poured into ice water (10 mL), stirred for 30 min., and then whole mixture was extracted with ethyl acetate (3×10 mL). The pH of the water solution was adjusted to 2 with HCl, the mixture was kept standing for 2 h and concentrated. The residue was purified on preparative HPLC column (Dynamax-300A C18 83 243 C, rate flow 20 mL/min.) with 0.1M TEAB followed by linear gradient of 0.1 TEAB/ag. acetonitrile (70%) to give (adenosin-5'-yl)methylenediphosphonate (452 mg, 72%) as his triethylammonium salt. This compound was identical with the corresponding sample prepared by the reaction of 5'-tosyl adenosine with tris(tetra-n-butylammonium)methylenediphosphonate (Example 6).

By following the same procedure, but using the corresponding nucleoside of Formula III instead of adenosine, the following methylenediphosphonates are prepared:

(2'-deoxyadenosin-5'-yl)methylenediphosphonate,
(2'-deoxy-2'-fluoroadenosin-5'-yl)methylenediphosphonate,
(3'-deoxy-3'-fluoroadenosin-5'-yl)methylenediphosphonate, and
[9-(2'-deoxy-2'-fluoro-β-D-arabinofuranosyl)adenine-5'-yl]methylenediphosphonate.

EXAMPLE 5

(5-β-D-Ribofuranosyl3-carboxyamidopyridine-5'-yl)difluoromethylenediphosphonate

The 2',3'-O-isopropylidene-5-β-D-ribofuranosyl3-carboxyamidopyridine (293 mg, 1 mmol), obtained as in Example 4, was dissolved in methylene chloride (6 mL), and then dimethylaminopyridine (122 mg, 1 mmol), triethylamine (202 mg, 2 mmol) and tosyl chloride (220, 1.2 mmol) was added. The mixture was stirred for 2 h and concentrated in vacuo. The residue was chromatographed on a column of silica gel with chloroform-ethanol (50:1, v/v) as the eluent to give 5'-O-tosyl derivative (410 mg, 92%). $^1$H NMR (CDCl$_3$) δ1.34 (s, 3H, iPr), 1.62 (s, 1H, iPr), 2.46 (s, 3H, Ts), 4.21 (dd, 1H, H5', $J_{4',5'}$=2.7 Hz, $J_{5',5''}$=10.8 Hz), 4.33–4.37 (m, 1H, H4'), 4.43 (dd, 1H, H5", $J_{4',5''}$=2.6 Hz), 4.54 (pseudot, 1H, H3'), 4.74 (dd, 1H, H2', $J_{1',2'}$=5.5 Hz, $J_{2',3'}$=3.4 Hz), 5.01 (d, 1H, H1'), 5.71 (brs, $^1$H, NH$_2$), 6.72 (brs, $^1$H, NH$_2$), 7.37 (d, 2H, Ts, J=8.4 Hz), 7.78 (d, 2H, Ts), 8.25 (s, 1H, H4), 8.68 (brs, 1H, H6), 9.12 (brs, 1H, H2) A solution of 2',3'-O-isopropylidene-5'-O-tosyl-5-β-D-ribofuranosyl3-carboxyamidopyridine (224 mg, 0.5 mmol) and tris(tetra-n-butylammonium)difluoromethylenediphosphonate (700 mg, 0.75 mmol) in dimethyl sulfoxide (10 mL) was kept standing for 2 h and lyophilized. The residue was dissolved in water and purified on preparative HPLC column as above to give 266 mg, 82% $^1$H NMR (D$_2$O) δ1.42 (s, 3H, iPr), 1.67 (s, 3H, iPr), 4.27–4.33 (m, 2H, H5', H5"), 4.45–4.48 (m, 1H, H4'), 4.80–4.87 (m, 1H, H3'), 5.05–5.12 (m, 2H, H1'H2'$J_{1',2'}$=5.7 Hz), 8.42 (s, 1H, H4), 8.73 (s, 1H, H6), 8.92 (s, 1H, H2). $^{31}$P NMR (D$_2$), δ4.12, 7.18 (part AB of ABX$_2$ system, $J_{A,B}$=52.0 Hz, $J_{A,X}$=88.5 Hz, $J_{B,X}$=73.2 Hz, X=F), $^{19}$F NMR (D$_2$) δ−53.61 (dd, 2F, $J_{P',F}$=88.5 Hz, $J_{P'',F}$=73.2 Hz).

By following the same procedure, but using the corresponding nucleoside of Formula II instead of 3-carboxyamidopyridine riboside, the following difluoromethylenediphosphonates are prepared:
(6-β-D-Ribofuranosyl2-carboxyamidopyridine-5'-yl)difluoromethylenediphosphonate,
(2-β-D-Ribofuranosyl4-carboxyamidopyridine-5'-yl)difluoromethylenediphosphonate,
(5-β-D-Ribofuranosyl-3-cyanopyridine-5'-yl)difluoromethylenediphosphonate,
(6-β-D-Ribofuranosyl-2-cyanopyridine-5'-yl)difluoromethylenediphosphonate, and
(2-(β-D-Ribofuranosyl-4-cyanopyridine-5'-yl)difluoromethylenediphosphonate.

EXAMPLE 6

(Adenosin-5'-yl)difluroromethylenediphosphonate

5'-O-Tosyladenosine (421, 1 mmol) was treated with tris(terta-n-butylammonium)difluoromethylenediphosphonate as described in Example 5 to give the (adenosine-5-yl)difluoromethylenediphosphonate in 64% yield.

By following the same procedure, but using the corresponding nucleoside of Formula III instead of adenosine, the following difluoromethylenediphosphonates are prepared:
(2'-deoxyadenosin-5'-yl)difluoromethylenediphosphonate,
(2'-deoxy-2'-fluoroadenosin-5'-yl)difluoromethylenediphosphonate,
(3'-deoxy-3'-fluoroadenosin-5'-yl)difluoromethylenediphosphonate, and
[9-(2'-deoxy-2'-fluoro-β-D-arabinofuranosyl)adenine-5'-yl]difluoromethylenediphosphonate.

EXAMPLE 7

P$^1$-[5-(β-D-Ribofuranosyl)3-carboxyamidopyridine-5'-yl]-P$^2$-[adenosine-5"-yl]methylenediphosphonate and P$^1$-[(5-β-D-ribofuranosyl)-3-cyanopyridine-5'-yl]-P$^2$-[adenosine-5'-yl]methylene-diphosphonate.

(Adenosin-5'-yl)methylenediphosphonate (obtained as in Example 4, . . . , 1 mmol) was dissolved in a mixture of DMSO (20 mL) and triethyl orthoformate (3.9 mL) and trifluoroacetic acid (5 mL) was added. The mixture was stirred for 16 h and lyophilized. The residue was treated with ethyl ether (100 mL). The precipitate was collected by centrifugation and dried at reduced pressure. This product was suspended in pyridine (16 mL) containing tri-n-butyl amine (2.5 mL) and 2',3'-O-isopropylidene-5-β-D-ribofuranose-3-carboxyamidopyridine (obtained as in Example 3, 322 mg, 1.1 mmol) and dicyclohexylcarbodiimide (DCC, 1.0 g) was added. The reaction was stirred for 4 days and concentrated in vacuo. The residue was suspended in water (100 mL), filtered and the filtrate was treated with Dowex 50W (H$^+$) for 8 h. The resin was filtered, the filtrate was concentrated in vacuo and the residue was purified on preparative HPLC column as described before to give the β-methylene CNAD as triethylammonium salt, which was converted to the disodium salt by passing trough Dowex 50W (Na$^+$) to give (60 mg, 10%). $^1$H NMR (D$_2$O) δ2.28 (t, 2H, CH$_2$ $J_{P,H}$=20.1 Hz), 4.05–4.40 [m, 8H, H3',4',5',5"(adenosine), H3',4',5',5" (3-carboxyamidopyridine riboside)], 4.50 [pseudot, 1H, H2' (NR)], 4.70 [pseudot, 1H, H2'(A)], 4.87 [d, 1H, H1'(NR), $J_{1',2'}$=4.9 Hz],6.02 [d, 1H, H1' (A), $J_{1',2'}$=5.2 Hz], 8.17 [s, 1H, H4 (NR)], 8.20, 8.45 [two 1H singlets, H2, H8 (A)], 8.59 [brs, 1H, H6(NR)],8.75 [brs, 1H, H2 (NR)]. $^{31}$P NMR (D$_2$O) δ17.63, 17.88 (AB system, $J_{A,B}$=10.4 Hz).

Due to dehydration (DCC) of the desired product, the P$^1$-[(5-β-D-ribofuranosyl)-3-cyanopyridine-5'-yl]-P$^2$-[adenosine-5'-yl]methylenediphosphonate (70 mg 14%) was also obtained. $^1$H NMR (D$_2$O) δ2.28 (t, 2H, CH$_2$, $J_{P,H}$= 20.1 Hz), 4.02–4.42 [m, 8H, H3',4',5',5" (adenosine), H3',4',5',5" (3-carboxyamidopyridine riboside)], 4.55 [pseudot, 1H, H2' (NR)], 4.74 [pseudot, 1H, H2'(A)], 4.79 [d, 1H, H,'(NR), $J_{1',2'}$=4.9 Hz], 6.06 [d, 1H, H1' (A), $J_{1',2'}$=5.4 Hz], 8.17 [s, 1H, H4 (NR)], 8.20, 8.50 [two 1H singlets, H2, H8 (A)], 8.69 [s, 1H, H6 (NR)], 8.71 [s, 1H, H2 (NR)]. $^{31}$P NMR (D$_2$O) δ17.63, 17.88 (AB system, $J_{A,B}$=9.9 Hz).

By following the same procedure, but using the corresponding methylenediphosphonates of the compound of Formula III instead of (adenosin-5'-yl)methylenediphosphonate and nucleosides of Formula II, the following dinucleotides are prepared:
P$^1$-[6-(β-D-Ribofuranosyl)2-carboxyamidopyridine-5'-yl]-P$^2$-[adenosine -5"-yl]methylenediphosphonate,
P$^1$-[2-(β-D-Ribofuranosyl)4-carboxyamidopyridine-5'-yl]-P$^2$-[adenosine-5"-yl]methylenediphosphonate, P$^1$-[5-(β-D-Ribofuranosyl)-3-cyanopyridine-5'-yl]-P$^2$-[adenosine-5"-yl]-methylenediphosphonate,
P$^1$-[6-(β-D-Ribofuranosyl)-2-cyanopyridine-5'-yl]-P$^2$-[adenosine-5"-yl]-methylenediphosphonate,
P$^1$-[2-(β-D-Ribofuranosyl)-4-cyanopyridine-5'-yl]-P$^2$-[adenosine-5"-yl]methylenediphosphonate.
P$^1$-[5-(β-D-Ribofuranosyl)3-carboxyamidopyridine-5'-yl]-P$^2$-[2'-deoxyadenosine-5"-yl]methylenediphosphonate,
P$^1$-[6-(β-D-Ribofuranosyl)2-carboxyamidopryidine-5'-yl]-P$^2$-[2'-deoxyadenosine-5"-yl]methylenediphosphonate,
P$^1$-[2-(β-D-Ribofuranosyl)4-carboxyamidopryidine-5'-yl]-P$^2$-[2'-deoxyadenosine-5"-yl]methylenediphosphonate,
P$^1$-[5-(β-D-Ribofuranosyl)-3-cyanopyridine-5'-yl]P$^2$-[2'-deoxyadenosine-5"-yl]methylenediphosphonate,
P$^1$-[6-(β-D-Ribofuranosyl)-2-cyanopyridine-5'-yl]-P$^2$-2'-deoxyadenosine-5"-yl]methylenediphosphonate,
P$^1$-[2-(β-D-Ribofuranosyl)-4-cyanopyridine-5'-yl]-P$^2$-[2'-deoxyadenosine-5"-yl]methylenediphosphonate,
P$^1$-[5-(β-D-Ribofuranosyl)3-carboxyamidopyridine-5'-yl]-P$^2$-[2'-deoxy-2'-fluoroadenosine-5"-yl]methylenediphosphonate,
P$^1$-[6-(β-D-Ribofuranosyl)2-carboxyamidopyridine-5'-yl]-P$^2$-[2'-deoxy-2'-fluoroadenosine-5"-yl]methylenediphosphonate,
P$^1$-[2-(β-D-Ribofuranosyl)4-carboxyamidopyridine-5'-yl]-P$^2$-[2'-deoxy-2'-fluoroadenosine-5"-yl]methylenediphosphonate, P¹-[5-(β-D-Ribofuranosyl)-3-cyanopyridine-5'-yl]-P²-[2'-deoxy-2'-fluoroadenosine-5"-yl]methylenediphosphonate, P¹-[6-(β-D-Ribofuranosyl)-2-cyanopyridine-5'-yl]-P²-[2'-deoxy-2'-fluoroadenosine-5"-yl]methylenediphosphonate, P¹-[2-(β-D-Ribofuranosyl)-4-cyanopyridine-5'-yl]-P²-[2'-deoxy-2'-fluoroadenosine-5"-yl]methylenediphosphonate, P¹-[5-(β-D-Ribofuranosyl)3-carboxyamidopyridine-5'-yl]-P²-[3'-deoxy-3'-fluoroadenosine-5"-yl]methylenediphosphonate, P¹-[6-(β-D-Ribofuranosyl)2-carboxyamidopyridine-5'-yl]-P²-[3'-deoxy-3'-fluoroadenosine-5"-yl]methylenediphosphonate, P¹-[(β-D-Ribofuranosyl)4carboxyamidopyridine-5'-yl]-P²-[3'-deoxy-3'-fluoroadenosine-5"-yl]methylenediphosphonate, P¹-[5-(β-D-Ribofuranosyl)-3-cyanopyridine-5'-yl]-P²-[3'-deoxy-3'-fluoroadenosine-5"-yl]methylenediphosphonate, P¹-[6-(β-D-Ribofuranosyl)-2-cyanopyridine-5'-yl]-P²-[3'-deoxy-3'-fluoroadenosine-5"-yl]methylenediphosphonate, P¹-[2-(β-D-Ribofuranosyl)-4-cyanopyridine-5'-yl]-P²-[3-deoxy-3'-fluoroadenosine-5"-yl]methylenediphosphonate, P¹-[5-(β-D-Ribofuranosyl)3-carboxyamidopyridine-5'-yl]-P²-[9-(2'-deoxy-2'-fluoro-β-D-arabinofuranosyl)adenine-5"-yl]methylenediphosphonate, P¹-[6-(β-D-Ribofuranosyl)2-carboxyamidopyridine-5'-yl]-P²-[9-(2'-deoxy-2'-fluoro-β-D-arabinofuranosyl)adenine-5"-yl]methylenediphosphonate, P¹-[2-(β-D-Ribofuranosyl)4-carboxyamidopyridine-5'-yl]-P²-[9-(2'-deoxy-2'-fluoro-β-D-arabinofuranosyl)adenine-5"-yl]methylenediphosphonate, P¹-[5-(β-D-Ribofuranosyl)3-cyanopyridine-5'-yl]-P²-[9-(2'-deoxy-2'-fluoro-β-D-arabinofuranosyl)adenine-5"-yl]methylenediphosphonate, P¹-[6-(β-D-Ribofuranosyl)-2-cyanopyridine-5'-yl]-P²-[9-(2'-deoxy-2'-fluoro-β-D-arabinofuranosyl)adenine-5"-yl]methylenediphosphonate, and P¹-[2-(β-D-Ribofuranosyl)-4-cyanopyridine-5'-yl]-P²-[9-(2'-deoxy-2'-fluoro-β-D-arabinofuranosyl)adenine-5"-yl]methylenediphosphonate.

EXAMPLE 8

P¹-[5-(β-D-Ribofuranosyl)3-carboxyamidopyridine-5'-yl]-P²-[adenosine-5"-yl]difluoromethylenedi-phosphonate.

The (2',3'-O-isopropylidene-5-β-D-ribofuranosyl3-carboxyamidopyridine-5'-yl)difluoromethylenediphosphonate (obtained as in Example 5, 649 mg, 1 mmol) was coupled with 2',3'-O-isopropylidene adenosine (4.6 g, 15 mmol) in the same manner as above to give β-difluoromethylene CNAD (50, 7%) ¹H NMR (D₂O) 4.05–4.40 (m, 8H, H3', H4', H5', H5" -A and NR), 4.53 (pseudot, 1H, H2' (NR), 468 (pseudot, 1H (A), 4.90 (d, 1H, H1' (NR), J₁',₂=5.1 Hz ), 5.99 (d, 1H, H1' (A), J₁',₂=5.3 Hz), 8.21 (s, 1H, H4 (NR)], 8.26, 8.50 [two 1H singlets, H2, H8 (A)], 8.61 (s, 1H, H6 (NR)], 8.80 (s, 1H, H2 (NR)].

³¹P NMR (D₂O) δ4.02, 4.36 (AB part of ABX₂ system, J_{A,B}=55.3 Hz, J_{A,X}=83.1 Hz, J_{B,X}=83.5 Hz, X=F).

By following the same procedure, but using the corresponding difluoromethylenediphosphonate derivative of the compound of Formula II instead of (5-β-D-ribofuranosyl3-carboxyamidopyridine-5'-yl)difluoromethylenediphosphonate and nucleosides of Formula III, the following dinucleotides are prepared:

P¹-[6-(β-D-Ribofuranosyl)2-carboxyamidopyridine-5'-yl]-P²-[adenosine-5"-yl]difluoromethylenediphosphonate, P¹-[2-(β-D-Ribofuranosyl)4-carboxyamidopyridine-5'-yl]-P²-[adenosine-5"-yl]difluoromethylenediphosphonate, P¹-[5-(β-D-Ribofuranosyl)-3-cyanopyridine-5'-yl]-P²-[adenosine-5"-yl]difluoromethylenediphosphonate, P¹-[6-(β-D-Ribofuranosyl)-2-cyanopyridine-5'-yl]-P²-[adenosine-5"-yl]difluoromethylenediphosphonate, P¹-[2-(β-D-Ribofuranosyl)-4-cyanopyridine-5'-yl]-P²-[adenosine-5"-yl]difluoromethylenediphosphonate, P¹-[5-(β-D-Ribofuranosyl)3-carboxyamidopyridine-5'-yl]-P²-[2'-deoxyadenosine-5"-yl]difluoromethylenediphosphonate, P¹-[6-(β-D-Ribofuranosyl)2-carboxyamidopyridine-5'-yl]-P²-[2'-deoxyadenosine-5"-yl]difluoromethylenediphosphonate, P¹-[2-(β-D-Ribofuranosyl)4-carboxyamidopyridine-5'-yl]-P²-[2'-deoxyadenosine-5"-yl]difluoromethylenediphosphonate, P¹-[5-(β-D-Ribofuranosyl)-3-cyanopyridine-5'-yl]-P²-[2'-deoxyadenosine-5"-yl]difluoromethylenediphosphonate, P¹-[6-(β-D-Ribofuranosyl)-2-cyanopyridine-5'-yl]-P²-2'-deoxyadenosine-5"-yl]difluoromethylenediphosphonate, P¹-[2-(β-D-Ribofuranosyl)-4-cyanopyridine-5'-yl]-P²-[2'-deoxyadenosine-5"-yl]difluoromethylenediphosphonate, P¹-[5-(β-D-Ribofuranosyl)3-carboxyamidopyridine-5'-yl]-P²-[2'-deoxy-2'-fluoroadenosine-5"-yl]difluoromethylenediphosphonate, P¹-[6-(β-D-Ribofuranosyl)2-carboxyamidopyridine-5'-yl]-P²-[2'-deoxy-2'-fluoroadenosine-5"-yl]difluoromethylenediphosphonate, P¹-[2-(β-D-Ribofuranosyl)4-carboxyamidopyridine-5'-yl]-P²-[2'-deoxy-2'-fluoroadenosine-5"-yl]difluoromethylenediphosphonate, P¹-[5-(β-D-Ribofuranosyl)-3-cyanopyridine-5'-yl]-P²-[2'-deoxy-2'-fluoroadenosine-5"yl]difluoromethylenediphosphonate, P¹-[6-(β-D-Ribofuranosyl)-2-cyanopyridine-5'-yl]-P²-[2'-deoxy-2'-fluoroadenosine-5"-yl]difluoromethylenediphosphonate, P¹-[2-(β-D-Ribofuranosyl)-4-cyanopyridine-5'-yl]-P²-[2'-deoxy-2'-fluoroadenosine-5"-yl]difluoromethylenediphosphonate, P¹-[5-(β-D-Ribofuranosyl)3-carboxyamidopyridine-5'-yl]-P²-[3'-deoxy-3'-fluoroadenosine-5"-yl]difluoromethylenediphosphonate, P¹-[6-(β-D-Ribofuranosyl)2-carboxyamidopyridine-5'-yl]-P²-[3'-deoxy-3'-fluoroadenosine-5"-yl]difluoromethylenediphosphonate, P¹-(β-D-Ribofuranosyl)4-carboxyamidopyridine-5'-yl-P²-3'-deoxy-3'-fluoroadenosine-5"-yl-fluoro]difluoromethylenediphosphonate, P¹-[5-(β-D-Ribofuranosyl)-3-cyanopyridine-5'-yl]-P²-[3'-deoxy-3'-fluoroadenosine-5"-yl]difluoromethylenediphosphonate, P¹-[6-(β-D-Ribofuranosyl)-2-cyanopyridine-5'-yl]-P²-[3'-deoxy-3'-fluoroadenosine-5"-yl]difluoromethylenediphosphonate, P¹-[2-(β-D-Ribofuranosyl)-4-cyanopyridine-5'-yl]-P²-[3'-deoxy-3'-fluoroadenosine-5"-yl]difluoromethylenediphosphonate, P¹-[5-(β-D-Ribofuranosyl)3-carboxyamidopyridine-5'-yl]-P²-[9-(2'-deoxy-2'-fluoro-β-D-arabino-furanosyl)]adenine-5"-yl]difluoromethylenediphosphonate, P¹-[6-(β-D-Ribofuranosyl)2-carboxyamidopyridine-5'-yl]-P²-[9-(2'-deoxy-2'-fluoro-β-D-arabino-furanosyl)]adenine-5"-yl]difluoromethylenediphosphonate, P¹-[2-(β-D-Ribofuranosyl)4-carboxyamidopyridine-5'-yl]-P²-[9-(2'-deoxy-2'-fluoro-β-D-arabino-furanosyl)adenine-5"-yl]difluoromethylenediphosphonate, P¹-[5-(β-D-Ribofuranosyl)-3-cyanopyridine-5'-yl]-P²-[9-(2'-deoxy-2'-fluoro-β-D-arabino-furanosyl)adenine-5"-yl]difluoromethylenediphosphonate, P$^1$-[6-(β-D-Ribofuranosyl)-2-cyanopyridine-5'-yl]-P$^2$-[9-(2'-deoxy-2'-fluoro-β-D-arabino-furanosyl)adenine-5"-yl]difluoromethylenediphosphonate, and
P$^1$-[2-(β-D-Ribofuranosyl)-4-cyanopyridine-5'-yl]-P$^2$-[9-(2'-deoxy-2'-fluoro-β-D-arabino-furanosyl)adenine-5"-yl]difluoromethylenediphosphonate.

Biological Activity

1. Cytotoxicity of 5-(β-D-ribofuranosyl)3-carboxyamidopyridine-(5'-5")-adenosine pyrophosphate (2, CNAD) to murine leukemia L1210 cells.

Murine leukemia L1210 cells were grown in RPMI 1640 medium. Logarithmically growing cells were incubated with various concentrations of CMAD for 24 and 48 hr periods and the cytotoxicity determined by counting the cells in a Coulter counter.

It was found that the 5-(β-D-ribofuranosyl)3-carboxyamidopyridine-(5'-5")-adenosine pyrophosphate (2, CNAD) inhibits the proliferation of L1210 cells by 50% (IC$_{50}$) at the concentration of 7 μM.

2. Inhibition of horse liver alcohol dehydrogenase (ADH) and bovine glutamate dehydrogenase (GDH)

Rate measurements for each of the dehydrogenases used in this study are based on the spectral properties of NADH. In assays with NAD as a substrate, rates were determined by measuring the increase in absorbance at 340 nm resulting from the conversion of NAD to NADH. Rates, using absorbance measurements, were calculated using a millimolar extinction coefficient of 6.22/cm for NADH.

Alcohol dehydrogenase assays were run at pH 8.0, using 0.1M sodium phosphate buffer. Glutamate dehydrogenase assays were at pH 7.0 in 0.1M sodium phosphate buffer, containing 10 μm EDTA. All kinetic assays were run at least in duplicate.

Initial values of inhibition constants were estimated from Linewever-Burk plots, using linear regression to obtain values for the slope and intercept of each line. Inhibition was judged to be competitive if the values obtained for the intercepts of the appropriate polots differed by less than three standard deviations as determined by linear regression. Values for the inhibition constant, $K_{is}$ was obtained using the relationship:

$$K_{is}=[I]/\{[S(+)/S(-)]-1\}$$

where $S(+)$ and $S(-)$ are the slopes of the plots in the presence and absence of inhibitor, respectively, and [I] is the concentration of total added inhibitor. Where a noncompetitive pattern of inhibition was observed, a similar analysis was used to obtain $K_{ii}$. $K_m$ for conenzyme was obtained from the slope and intercept obtained in plots in the absence of inhibitor, using the relationship: $K_m$=Slope/$V_{max}$.

Values of effective inhibition constants and patterns of inhibition for CNAD binding to ADH were obtained by direct least-squares fits to the nonreciprocal forms of the Michaelis-Menten rate equations. Kinetic data were fit to the following relationships, assuming both competitive and non-competitive inhibition respectively:

$$v_o=V_m[A]/\{K_m(1+[I]/K_{is})+[A]\}$$

or $$v_o=V_m[A]/\{K_m(1+[I]/K_{is})+[A](1+[I]/K_{ii})\}$$

Where $v_o$ is the initial reaction rate, $V_m$ is the maximal rate, and $K_m$ and [A] the Michaelis constant and concentration of the variable substrate, respectively. The pattern of inhibition considered to best account for the observed data was that giving both the smallest residuals between observed and calculated values, and the smallest standard errors in the computed kinetics constants. This method demonstrated non-competitive inhibition of ADH with respect to NAD by CNAD with an apparent $K_i$ ($K_{i'}$) of 6 nM.

In order to estimate the magnitude of nonlinear effects introduced by tight binding by CNAD, apparent $K_i$'s with respect to NAD were also obtained by a fit of kinetic data to Sculley and Morrison's nonlinear rate equation:

$$v_o = \frac{k_{cat}[A]}{2(K_m+[A])}[\{([E]-[I]-K_i)^2+4K_i\}^{1/2}-(K_i+[I]-[E])]$$

where [E] is the total enzyme concentration, $k_{cat}$ is the maximum rate of product formation and, in this case, [A] is the concentration and Km the Michaelis constant of NAD. Derivation of this rate equation assumes the presence of a tight binding inhibitor, i.e., that [I]~[E].

In this experiment both inhibitor and enzyme concentration were varied. Initial rates $v_o$ were measured at total concentrations of CNAD ([I]) of 0, 2.4, 9.6, and 19.2 nM over four concentrations of ADH ([E]). Concentrations of ethanol and NAD were fixed at 1.2 nM and 87 μM at pH 8.0. The apparent inhibition constant with respect to NAD, $K_{i'}$, was then obtained by non-linear least-squares fit to the rate equation under the array of experimental conditions employed. The true rate constant $K_i$ was obtained from the apparent rate constant $K_i$ was obtained from the apparent rate constant $K_{i'}$ via the relationship:

$$K_i=K_{i'}/(1+[A]/K_m)$$

Results for 6-(β-D-ribofuranosyl)picolinamide-(5'-5")adenosine pyrophosphate (C-PAD) indicate competitive inhibition of ADH with respect to NAD, with $K_i$=20 μM. The results for CNAD, however, showed competitive inhibition of GDH ($K_i$=15 μM), but non-competitive inhibition of ADH, with $K_i$=2 nM.

Discussion

Inhibition of alcohol dehydrogenase (ADH) provides potential therapies for ethylene glycol intoxication, ethanol-induced hypoglycemia and lactacidemia and methanol poisoning. This along with the extensive structural information available about the enzyme and its complexes, have made ADH an attractive target for inhibitor design. A number of classes of highly potent reversible ADH-inhibitors have been developed. These are 4-substituted alkylpyrazoles, 1-mercapto-n-alkanes, phenylacetamide and formamide derivatives and adloximes. Like CNAD, these inhibitors bind the catalytic site Zn via a nitrogen, oxygen or sulfur ligand. Unlike CNAD, these compounds act as substrate analogues, binding Zn from the substrate site, with alkyl or phenyl groups extending into the hydrophobic substrate cleft. Inhibitors of this type can bind internary complexes with cofactor, forming a secondary ligand to the nicotinamide ring. NAD analogues have been developed as inactivating affinity labels, forming covalent interactions with active site residues. However, CNAD is the first cofactor analogue which reversibly interacts with the catalytic Zn.

Similar selectivity for these compounds is asserted for inosine monophosphate dehydrogenase (IMPDH). As a result, such NAD analogues should be valuable in cancer treatment. NAD-analogues, not nucleosides, that are able to penetrate the cell membrane may be of therapeutic interest since nucleosides related to nicotinamide riboside are not effectively metabolized into their corresponding NAD-analogues. They do not require metabolic activation by cellular enzymes.

What is claimed is:
1. A compound having the structure:

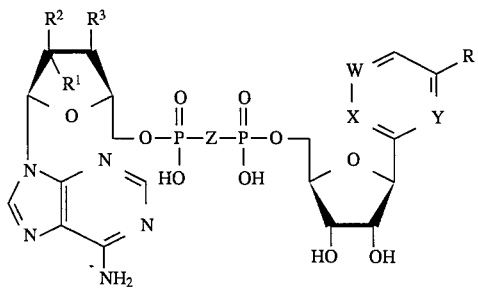

wherein $R^1$, $R^2$, and $R^3$ are same or different, and are hydrogen, hydroxyl, or fluorine; Z is O, $CH_2$ or $CF_2$; R is chlorine, bromine, iodine, carbonitrile, carboxylic ester, or carboxamide; and one of W, X and Y is N or $N^+R'$, wherein R' is methyl or ethyl, and all others are CH; provided that $R^1$ is not H when $R^2$ and $R^3$ are OH, Z is O, R is carboxamide and W is N or $N^+R'$.

2. A compound of claim 1 selected from the group consisting of:
5-(β-D-Ribofuranosyl)3-carboxyamidopyridine-(5'-5")-adenosine pyrophosphate,
6-(β-D-Ribofuranosyl)2-carboxyamidopyridine-(5'-5")-adenosine pyrophosphate,
2-(β-D-Ribofuranosyl)4-carboxyamidopyridine-(5'-5")-adenosine pyrophosphate,
5-(β-D-Ribofuranosyl)-3-cyanopyridine-(5'-5")-adenosine pyrophosphate,
6-(β-D-Ribofuranosyl)-2-cyanopyridine-(5'-5")-adenosine pyrophosphate,
2-(β-D-Ribofuranosyl)-4-cyanopyridine-(5'-5")-adenosine pyrophosphate,
5-(β-D-Ribofuranosyl)3-carboxyamidopyridine-(5'-5")-2'-deoxyadenosine pyrophosphate,
6-(β-D-Ribofuranosyl)2-carboxyamidopyridine-(5'-5")-2'-deoxyadenosine pyrophosphate,
2-(β-D-Ribofuranosyl)4-carboxyamidopyridine-(5'-5")-2'-deoxyadenosine pyrophosphate,
5-(β-D-Ribofuranosyl)-3-cyanopyridine-(5'-5")-2'-deoxyadenosine pyrophosphate,
6-(β-D-Ribofuranosyl)-2-cyanopyridine-(5'-5")-2'-deoxyadenosine pyrophosphate,
2-(β-D-Ribofuranosyl)-4-cyanopyridine-(5'-5")-2'-deoxyadenosine pyrophosphate,
5-(β-D-Ribofuranosyl)3-carboxyamidopyridine-(5'-5")-2'-deoxy -2'-fluoroadenosine pyrophosphate,
6-(β-D-Ribofuranosyl)2-carboxyamidopyridine-(5'-5")-2"-deoxy-2"-fluoroadenosine pyrophosphate,
2-(β-D-Ribofuranosyl)4-carboxyamidopyridine-(5'-5")-2'-deoxy-2'-fluoroadenosine pyrophosphate,
5-(β-D-Ribofuranosyl)-3-cyanopyridine-(5'-5")-2'-deoxy-2'-fluoroadenosine pyrophosphate,
6-(β-D-Ribofuranosyl)-2-cyanopyridine-(5'-5")-2'-deoxy-2'-fluoroadenosine pyrophosphate,
2-(β-D-Ribofuranosyl)-4-cyanopyridine-(5'-5")-2'-deoxy-2'-fluoroadenosine pyrophosphate,
5-(β-D-Ribofuranosyl)3-carboxyamidopyridine-(5'-5")-3'-deoxy-3'-fluoroadenosine pyrophosphate,
6-(β-D-Ribofuranosyl)2-carboxyamidopyridine-(5'-5")-3'-deoxy-3'-fluoroadenosine pyrophosphate,
2-(β-D-Ribofuranosyl)4-carboxyamidopyridine-(5'-5")-3'-deoxy-3'-fluoroadenosine pyrophosphate,
5-(β-D-Ribofuranosyl)-3-cyanopyridine-(5'-5")-3'-deoxy-3'-fluoroadenosine pyrophosphate,
6-(β-D-Ribofuranosyl)-2-cyanopyridine-(5'-5")-3'-deoxy-3'-fluoroadenosine pyrophosphate,
2-(β-D-Ribofuranosyl)-4-cyanopyridine-(5'-5")-3'-deoxy-3'-fluoroadenosine pyrophosphate,
-5-(β-D-Ribofuranosyl)3-carboxyamidopyridine-(5'-5")-9-(2'-deoxy-2'-fluoro-β-D-arabinofuranosyl)-adenine pyrophosphate,
6-(β-D-Ribofuranosyl)2-carboxyamidopyridine-(5'-5")-9-(2'-deoxy-2'-fluoro-β-D-arabinofuranosyl)-adenine pyrophosphate,
2-(β-D-Ribofuranosyl)4-carboxyamidopyridine-(5'-5")-9-(2'-deoxy-2'-fluoro-β-D-arabinofuranosyl)-adenine pyrophosphate,
5-(β-D-Ribofuranosyl)-3-cyanopyridine-(5'-5")-9-(2'-deoxy-2'-fluoro-β-D-arabinofuranosyl)-adenine pyrophosphate,
6-(β-D-Ribofuranosyl)-2-cyanopyridine-(5'-5")-9-(2'-deoxy-2'-fluoro-β-D-arabinofuranosyl)-adenine pyrophosphate, and
2-(β-D-Ribofuranosyl)-4-cyanopyridine-(5'-5")-9-(2'-deoxy-2'-fluoro-β-D-arabinofuranosyl)-adenine pyrophosphate.

3. A compound of claim 1 selected from the group consisting of:
$P^1$-[5-(β-D-Ribofuranosyl)3-carboxyamidopyridine-5'-yl]-$P^2$-[adenosine-5"-yl]methylenediphosphonate,
$P^1$-[6-(β-D-Ribofuranosyl)2-carboxyamidopyridine-5'-yl]-$P^2$-[adenosine-5"-yl]-methylenediphosphonate,
$P^1$-[2-(β-D-Ribofuranosyl)4-carboxyamidopyridine-5'-yl]-$P^2$-[adenosine-5"-yl]methylenediphosphonate,
$P^1$-[5-(β-D-Ribofuranosyl)-3-cyanopyridine-5'-yl]-$P^2$-[adenosine-5"-yl]methylenediphosphonate,
$P^1$-[6-(β-D-Ribofuranosyl)-2-cyanopyridine-5'-yl]-$P^2$-[adenosine-5"-yl]methylenediphosphonate,
$P^1$-[2-(β-D-Ribofuranosyl)-4-cyanopyridine-5'-yl]-$P^2$-[adenosine-5"-yl]methylenediphosphonate,
$P^1$-[5-(β-D-Ribofuranosyl)3-carboxyamidopyridine-5'-yl]-$P^2$-[2'-deoxyadenosine-5"-yl]methylenediphosphonate,
$P^1$-[6-(β-D-Ribofuranosyl)2-carboxyamidopyridine-5'-yl]-$P^2$-deoxyadenosine-5"-yl]-methylenediphosphonate,
$P^1$-[2-(β-D-Ribofuranosyl)4-carboxyamidopyridine-5'-yl]-$P^2$-[2'-deoxyadenosine-5"-yl]methylenediphosphonate,
$P^1$-[5-(β-D-Ribofuranosyl)-3-cyanopyridine-5'-yl]-$P^2$-[2'-deoxyadenosine-5"-yl]methylenediphosphonate,
$P^1$-[6-(β-D-Ribofuranosyl)-2-cyanopyridine-5'-yl]-$P^2$-2'-deoxyadenosine-5"-yl]methylenediphosphonate,
$P^1$-[2-(β-D-Ribofuranosyl)-4-cyanopyridine-5'-yl]-$P^2$-[2'-deoxyadenosine-5"-yl]methylenediphosphonate,
$P^1$-[5-(β-D-Ribofuranosyl)3-carboxyamidopyridine-5'-yl]-$P^2$-[2'-deoxy-2'-fluoroadenosine-5"-yl]methylenediphosphonate,
$P^1$-[6-(β-D-Ribofuranosyl)2-carboxyamidopyridine-5'-yl]-$P^2$-[2'-deoxy-2'-fluoroadenosine-5"-yl]methylenediphosphonate,
$P^1$-[2-(β-D-Ribofuranosyl)4-carboxyamidopyridine-5'-yl]-$P^2$-[2'-deoxy-2'-fluoroadenosine-5"-yl]methylenediphosphonate,
$P^1$-[5-(β-D-Ribofuranosyl)-3-cyanopyridine-5'-yl]-$P^2$[2'-deoxy-2'-fluoroadenosine-5"-yl]-methylenediphosphonate,
$P^1$-[6-(β-D-Ribofuranosyl)-2-cyanopyridine-5'-yl]-$P^2$-[2'-deoxy-2'-fluoroadenosine-5"-yl]methylenediphosphonate,
$P^1$-[2-(β-D-Ribofuranosyl)-4-cyanopyridine-5'-yl]-$P^2$-[2'-deoxy-2'-fluoroadenosine-5"-yl]methylenediphosphonate,
$P^1$-[5-(β-D-Ribofuranosyl)3-carboxyamidopyridine-5'-yl]-$P^2$-[3'-deoxy-3'-fluoroadenosine-5"-yl]methylenediphosphonate,
$P^1$-[6-(β-D-Ribofuranosyl)2-carboxyamidopyridine-5'-yl]-$P^2$-[3'-deoxy-3'-fluoroadenosine-5"-yl]methylenediphosphonate,
$P^1$-[2-(β-D-Ribofuranosyl)4-carboxyamidopyridine-5'-yl]-$P^2$-[3'-deoxy-3'-fluoroadenosine-5"-yl]methylenediphosphonate, P¹-[5-(β-D-Ribofuranosyl)-3-cyanopyridine-5'-yl]-P²-[3'-deoxy-3'-fluoroadenosine-5"-yl]methylenediphosphonate,
P¹-[6-(β-D-Ribofuranosyl)-2-cyanopyridine-5'-yl]-P²-[3'-deoxy-3'-fluoroadenosine-5"-yl]methylenediphosphonate,
P¹-[2-(β-D-Ribofuranosyl)-4-cyanopyridine-5'-yl]-P²-[3'-deoxy-3'-fluoroadenosine-5"-yl]methylenediphosphonate,
P¹-[5-(β-D-Ribofuranosyl)3-carboxyamidopyridine-5'-yl]-P²-[9-(2'-deoxy-2'-fluoro-β-D-arabinofuranosyl)adenine-5"-yl]methylenediphosphonate,
P¹-[6-(β-D-Ribofuranosyl)2-carboxyamidopyridine-5'-yl]-P²-[9-(2'-deoxy-2'-fluoro-β-D-arabinofuranosyl)adenine-5-yl]methylenediphosphonate,
P¹-[2-(β-D-Ribofuranosyl)4-carboxyamidopyridine-5'-yl]-P²-[9-(2'-deoxy-2'-fluoro-β-D-arabinofuranosyl)adenine-5"-yl]methylenediphosphonate,
P¹-[5-(β-D-Ribofuranosyl)-3-cyanopyridine-5'-yl]-P²-[9-(2'-deoxy-2'-fluoro-β-D-arabinofuranosyl)adenine-5"-yl]methylenediphosphonate,
P¹-[6-(β-D-Ribofuranosyl)-2-cyanopyridine-5'-yl]-P²-[9-(2'-deoxy-2'-fluoro-β-D-arabinofuranosyl)adenine-5"-yl]methylenediphosphonate,
P¹-[2-(β-D-Ribofuranosyl)-4-cyanopyridine-5'-yl]-P²-[9-(2'-deoxy-2'-fluoro-β-D-arabinofuranosyl)-adenine-5"-yl]methylenediphosphonate,
P¹-[5-(β-D-Ribofuranosyl)3-carboxyamidopyridine-5'-yl]-P²-[adenosine-5"-yl]difluoromethylenediphosphonate,
P¹-[6-(β-D-Ribofuranosyl)2-carboxyamidopyridine-5'-yl]-P²-[adenosine-5"-yl]difluoromethylenediphosphonate,
P¹-[2-(β-D-Ribofuranosyl)4-carboxyamidopyridine-5'-yl]-P²-[adenosine-5"-yl]difluoromethylenediphosphonate,
P¹-[5-(β-D-Ribofuranosyl)-3-cyanopyridine-5'-yl]-P²-[adenosine-5"-yl]difluoromethylenediphosphonate,
P¹-[6-(β-D-Ribofuranosyl)-2-cyanopyridine-5'-yl]-P²-[adenosine-5"-yl]difluoromethylenediphosphonate,
P¹-[2-(β-D-Ribofuranosyl)-4-cyanopyridine-5'-yl]-P²-[adenosine-5"-yl]difluoromethylenediphosphonate,
P¹-[5-(β-D-Ribofuranosyl)3-carboxyamidopyridine-5'-yl]-P²-[2'-deoxyadenosine-5"-yl]difluoromethylenediphosphonate,
P¹-[6-(β-D-Ribofuranosyl)2-carboxyamidopyridine-5'-yl]-P²-[2'-deoxyadenosine-5"-yl]difluoromethylenediphosphonate,
P¹-[2-(β-D-Ribofuranosyl)4-carboxyamidopyridine-5'-yl]-P²-[2'-deoxyadenosine-5"-yl]difluoromethylenediphosphonate,
P¹-[5-(β-D-Ribofuranosyl)-3-cyanopyridine-5'-yl]-P²-[2'-deoxyadenosine-5"yl]difluoromethylenediphosphonate,
P¹-[6-(β-D-Ribofuranosyl)-2-cyanopyridine-5'-yl]-P²-2'-deoxyadenosine-5"yl]difluoromethylenediphosphonate,
P¹-[2-(β-D-Ribofuranosyl)-4-cyanopyridine-5'-yl]-P²-[2'-deoxyadenosine-5"yl]difluoromethylenediphosphonate,
P¹-[5-(β-D-Ribofuranosyl)3-carboxyamidopyridine-5'-yl]-P²-[2'-deoxy-2'-fluoroadenosine-5"yl]difluoromethylenediphosphonate,
P¹-[6-(β-D-Ribofuranosyl)2-carboxyamidopyridine-5'-yl]-P²-[2'-deoxy-2'-fluoroadenosine-5"yl]difluoromethylenediphosphonate,
P¹-[2-(β-D-Ribofuranosyl)3-carboxyamidopyridine-5'-yl]-P²-[2'-deoxy-2'-fluoroadenosine-5"-yl]difluoromethylenediphosphonate,
P¹-[5-(β-D-Ribofuranosyl)-3-cyanopyridine-5'-yl]-P²-[2'-deoxy-2'-fluoroadenosine-5"-yl]difluoromethylenediphosphonate,
P¹-[6-(β-D-Ribofuranosyl)-2-cyanopyridine-5'-yl]-P²-[2'-deoxy-2'-fluoroadenosine-5"-yl]difluoromethylenediphosphonate,
P¹-[2-(β-D-Ribofuranosyl)-4-cyanopyridine-5'-yl]-P²-[2'-deoxy-2'-fluoroadenosine-5"-yl]difluoromethylenediphosphonate,
P¹-[5-(β-D-Ribofuranosyl)3-carboxyamidopyridine-5'-yl]-P²-[3'-deoxy-3'-fluoroadenosine-5"-yl]difluoromethylenediphosphonate,
P¹-[6-(β-D-Ribofuranosyl)2-carboxyamidopyridine-5'-yl]-P²-[3'-deoxy-3'-fluoroadenosine-5"-yl]difluoromethylenediphosphonate,
P¹-(2-β-D-Ribofuranosyl)4-carboxyamidopyridine-5'-yl]-P²-3'-deoxy-3'-fluoroadenosine-5"-yl]difluoromethylenediphosphonate,
P¹-[5-(β-D-Ribofuranosyl)-3-cyanopyridine-5'-yl]-P²-[3'-deoxy-3'-fluoroadenosine-5"-yl]difluoromethylenediphosphonate,
P¹-[6-(β-D-Ribofuranosyl)-2-cyanopyridine-5'-yl]-P²-[3'-deoxy-3'-fluoroadenosine-5"-yl]difluoromethylenediphosphonate,
P¹-[2-(β-D-Ribofuranosyl)-4-cyanopyridine-5'-yl]-P²-[3'-deoxy-3'-fluoroadenosine-5"-yl]difluoromethylenediphosphonate,
P¹-[5-(β-D-Ribofuranosyl)3-carboxyamidopyridine-5'-yl]-P²-[9-(2'-deoxy-2'-fluoro-β-D-arabino-furanosyl)]adenine-5"-yl]-difluoromethylenediphosphonate,
P¹-[6-(β-D-Ribofuranosyl)2-carboxyamidopyridine-5'-yl]-P²-[9-(2'-deoxy-2'-fluoro-β-D-arabino-furanosyl)]adenine-5"-yl]-difluoromethylenediphosphonate,
P¹-[2-(β-D-Ribofuranosyl)4-carboxyamidopyridine-5'-yl]-P²-[9-(2'-deoxy-2'-fluoro-β-D-arabino-furanosyl)adenine-5"-yl]-difluoromethylenediphosphonate,
P¹-[5-(β-D-Ribofuranosyl)-3-cyanopyridine-5'-yl]-P²-[9-(2'-deoxy-2'-fluoro-β-D-arabino-furanosyl)-adenine-5"-yl]-difluoromethylenediphosphonate,
P¹-[6-(β-D-Ribofuranosyl)-2-cyanopyridine-5'-yl]-P²-[9-(2'-deoxy-2'-fluoro-β-D-arabino-furanosyl)-adenine-5"-yl]-difluoromethylenediphosphonate, and
P¹-[2-(β-D-Ribofuranosyl)-4-cyanopyridine-5'-yl]-P²-[9-(2'-deoxy-2'-fluoro-β-D-arabino-furanosyl)-adenine-5"-yl]-difluoromethylenediphosphonate.

4. A pharmaceutical composition which comprises the compound of claim 1 and a pharmaceutically acceptable carrier.

* * * * *